US011208486B2

United States Patent
Fang et al.

(10) Patent No.: US 11,208,486 B2
(45) Date of Patent: Dec. 28, 2021

(54) HUMAN PD-L1 ANTIBODIES

(71) Applicant: I-Mab Biopharma US Limited, Gaithersburg, MD (US)

(72) Inventors: Lei Fang, Shanghai (CN); Yuanyuan Yang, Shanghai (CN); Zhengyi Wang, Shanghai (CN); Bingshi Guo, Shanghai (CN); Feifei Cui, Shanghai (CN)

(73) Assignee: I-Mab Biopharma US Limited, Gaithersburg, MD (US)

( * ) Notice: Subject to any disclaimer, the term of this patent is extended or adjusted under 35 U.S.C. 154(b) by 0 days.

(21) Appl. No.: 17/277,909

(22) PCT Filed: Apr. 26, 2020

(86) PCT No.: PCT/CN2020/087019
§ 371 (c)(1),
(2) Date: Mar. 19, 2021

(87) PCT Pub. No.: WO2020/216379
PCT Pub. Date: Oct. 29, 2020

(65) Prior Publication Data
US 2021/0309747 A1 Oct. 7, 2021

(30) Foreign Application Priority Data
Apr. 26, 2019 (WO) ................ PCT/CN2019/084468

(51) Int. Cl.
| | | |
|---|---|---|
| *C07K 16/00* | (2006.01) | |
| *C07K 16/28* | (2006.01) | |
| *A61P 35/00* | (2006.01) | |
| *A61K 39/00* | (2006.01) | |

(52) U.S. Cl.
CPC .......... *C07K 16/2827* (2013.01); *A61P 35/00* (2018.01); *A61K 2039/505* (2013.01); *C07K 2317/21* (2013.01); *C07K 2317/31* (2013.01); *C07K 2317/565* (2013.01); *C07K 2317/76* (2013.01)

(58) Field of Classification Search
None
See application file for complete search history.

(56) References Cited

U.S. PATENT DOCUMENTS

2018/0334504 A1   11/2018   Qu et al.

FOREIGN PATENT DOCUMENTS

| CN | 105777906 A | 7/2016 |
| WO | 2013181634 A2 | 12/2013 |
| WO | 2014055897 A2 | 4/2014 |
| WO | 2017118321 A1 | 7/2017 |
| WO | WO2017118321 | * 7/2017 |
| WO | 2018005682 A2 | 1/2018 |

OTHER PUBLICATIONS

International Search Report and Written Opinion for PCT/CN087019 dated Jul. 29, 2020, 12 pages.

\* cited by examiner

*Primary Examiner* — Meera Natarajan
(74) *Attorney, Agent, or Firm* — Sheppard Mullin Richter & Hampton LLP

(57) ABSTRACT

Provided are full human anti-PD-L1 antibodies or fragments thereof. In various examples, the antibodies or fragments thereof include a VH CDR1, a VH CDR2, a VH CDR3, a VL CDR1, a VL CDR2, and a VL CDR3 which are selected from sequence groups of SEQ ID NO: 35-42, SEQ ID NO: 43-51, SEQ ID NO: 52-66, SEQ ID NO: 67-79, SEQ ID NO:80-88 and SEQ ID NO: 89-102, respectively, or variants of each thereof. Methods of using the antibodies or fragments thereof for treating and diagnosing diseases such as cancer and infectious diseases are also provided.

18 Claims, 5 Drawing Sheets
Specification includes a Sequence Listing.

HUMAN PD-L1 ANTIBODIES

This application is a U.S. National Stage Application under 35 U.S.C. 371 of International Application No. PCT/CN2020/087019, filed Apr. 26, 2020, which claims the benefit of International Application No. PCT/CN2019/084468, filed Apr. 26, 2019, the entire disclosure of each of which is hereby incorporated by reference.

SEQUENCE LISTING

The instant application contains a Sequence Listing which has been submitted in ASCII format via EFS-Web and is hereby incorporated by reference in its entirety. Said ASCII copy, created on Mar. 17, 2021, is named 296882_SL.txt and is 69 kilobytes in size.

BACKGROUND

Antibodies specific to programmed death-ligand 1 (PD-L1), also known as cluster of differentiation 274 (CD274) or B7 homolog 1 (B7-H1), are being used for cancer treatments and in other clinical applications. PD-L1 is a 40 kDa type 1 transmembrane protein believed to play a major role in suppressing the immune system during particular events such as pregnancy, tissue allografts, autoimmune disease and other disease states such as hepatitis. The binding of PD-L1 to PD-1 or B7.1 transmits an inhibitory signal which reduces the proliferation of CD8+ T cells at the lymph nodes and supplementary to that PD-1 is also able to control the accumulation of foreign antigen specific T cells in the lymph nodes through apoptosis which is further mediated by a lower regulation of the gene Bcl-2.

In addition to treatment of cancers, PD-L1 inhibition has also shown promises in treating infectious diseases. In a mouse model of intracellular infection, *L. monocytogenes* induced PD-L1 protein expression in T cells, NK cells, and macrophages. PD-L1 blockade (e.g., using blocking antibodies) resulted in increased mortality for infected mice. Blockade reduced TNFα and nitric oxide production by macrophages, reduced granzyme B production by NK cells, and decreased proliferation of *L. monocytogenes* antigen-specific CD8 T cells (but not CD4 T cells). This evidence suggests that PD-L1 acts as a positive costimulatory molecule in intracellular infection.

SUMMARY

The present disclosure provides anti-PD-L1 antibodies having high binding affinity to human PD-L1 proteins and can effectively block the interaction between PD-L1 and its receptor PD-1. The identified antibodies are fully human antibodies and are expected to have improved performance than humanized antibodies in clinical uses.

One embodiment of the present disclosure provides an anti-PD-L1 antibody or fragment thereof. In some embodiments, the antibody or antigen-binding fragment thereof comprises a VH CDR1 comprising an amino acid sequence selected from SEQ ID NO:35-42 and variants thereof having one or two amino acid substitution therefrom, a VH CDR2 comprising an amino acid sequence selected from SEQ ID NO:43-51 and variants thereof having one or two amino acid substitution therefrom, a VH CDR3 comprising an amino acid sequence selected from SEQ ID NO:52-66 and variants thereof having one or two amino acid substitution therefrom, a VL CDR1 comprising an amino acid sequence selected from SEQ ID NO:67-79 and variants thereof having one or two amino acid substitution therefrom, a VL CDR2 comprising an amino acid sequence selected from SEQ ID NO:80-88 and variants thereof having one or two amino acid substitution therefrom, and a VL CDR3 comprising an amino acid sequence selected from SEQ ID NO:89-102 and variants thereof having one or two amino acid substitution therefrom.

In one embodiment, the VH CDR1 comprises the amino acid sequence of SEQ ID NO:37, the VH CDR2 comprises the amino acid sequence of SEQ ID NO:46, 135, 136, 137, 142 or 143, the VH CDR3 comprises the amino acid sequence of SEQ ID NO:63, the VL CDR1 comprises the amino acid sequence of SEQ ID NO:76, the VL CDR2 comprises the amino acid sequence of SEQ ID NO:83, and the VL CDR3 comprises the amino acid sequence of SEQ ID NO:97. In a particular embodiment, the VH CDR2 comprises the amino acid sequence of SEQ ID NO:46.

In an example antibody or fragment, VH comprises the amino acid sequence of SEQ ID NO:23, 124, 126, 127, 128, 130, 140, or 145, and the VL comprises the amino acid sequence of SEQ ID NO:24 or 125, as well as their variants. For instance, the VH comprises the amino acid sequence of SEQ ID NO:124 or a first amino acid sequence having at least 95% sequence identity to SEQ ID NO:124 (while retaining the recited CDRs), and the VL comprises the amino acid sequence of SEQ ID NO: 125 or a second amino acid sequence having at least 95% sequence identity to SEQ ID NO:125 (while retaining the recited CDRs).

Also provided is a composition comprising the antibody or fragment thereof of and a pharmaceutically acceptable carrier. Still also provided is one or more polynucleotide encoding the antibody or fragment thereof, an isolated cell comprising one or more polynucleotide encoding the antibody or fragment thereof.

Treatment methods and uses are also provided. In one embodiment, a method of treating cancer or infection in a patient in need thereof is provided, comprising administering to the patient an effective amount of the antibody or fragment thereof of the present disclosure. In some embodiments, the cancer is a solid tumor. In some embodiments, the cancer is selected from the group consisting of bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer and thyroid cancer. In some embodiments, the cancer is selected from the group consisting of bladder cancer, liver cancer, pancreatic cancer, non-small cell lung cancer, breast cancer, urethral cancer, colorectal cancer, head and neck cancer, squamous cell cancer, Merkel cell carcinoma, gastrointestinal cancer, stomach cancer, oesophageal cancer, ovarian cancer, renal cancer, and small cell lung cancer. In some embodiments, the method further comprises administering to the patient a second cancer therapeutic agent. In some embodiments, the infection is viral infection, bacterial infection, fungal infection or infection by a parasite.

DETAILED DESCRIPTION

Definitions

Figure 1:
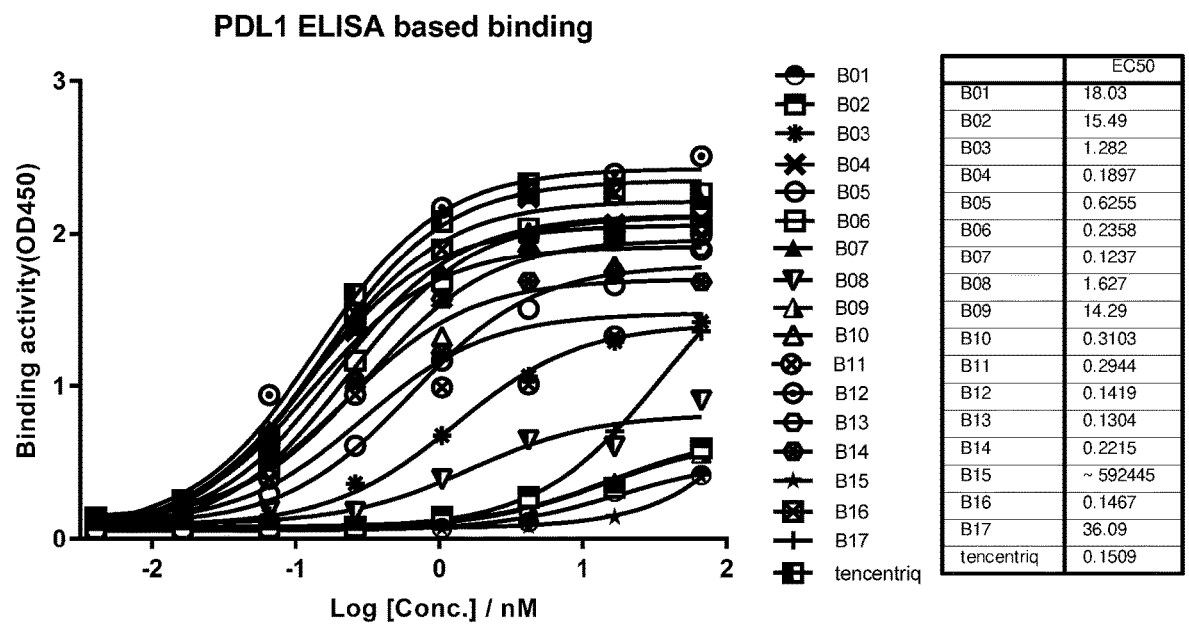
FIG. 1 shows the PD-L1 binding profiles of the tested antibodies.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG$_1$, IgG$_2$, IgG$_3$, IgG$_4$, IgG$_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab)$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-PD-L1 Antibodies

The present disclosure provides anti-PD-L1 antibodies, in particular fully human antibodies and fragments, with high affinity to the human PD-L1 protein. The tested antibodies exhibited potent binding and inhibitory activities and are useful for therapeutic and diagnostics uses.

As demonstrated in the experimental examples, a number of fully human anti-PD-L1 antibodies, including B01-B17, were obtained from phage libraries. Some of these antibodies exhibited excellent binding activities. For instance, B04, B05, B06, B07, B10, B11, B12, B13, B14 and B16 could dose dependently block the PD1/PD-L1 mediated NFAF-luciferase activity. Among them, B06, B12 and B16 were the most potent.

The antibodies of the present disclosure compare favorably to existing products on the market and in clinical development. Reference antibodies used include atezolizumab (Tecentrie™), a fully humanized, Fc-engineered monoclonal antibody of IgG1 isotype, and avelumab (Bavencio™), a fully human monoclonal antibody. Atezolizumab has been approved for the treatment of metastatic non-small cell lung cancer (NSCLC), extensive stage small cell lung cancer, and triple-negative breast cancer. Avelumab has been approved for the treatment of Merkel-cell carcinoma in the US and Europe. Atezolizumab and avelumab are the current leading PD-L1 antibodies on the market.

As shown in Example 1, quite a few tested antibodies, including B07, B12, B13 and B16 exhibited higher (or at least non-inferior) PD-L1 binding affinity than atezolizumab (FIG. 1). A variant of B12, B12-01, was further tested in comparison to atezolizumab and avelumab. Compared to B12, B12-01 had a serine substitution at the C-terminus of VH and a conventional DIQM stretch at the N-terminus of the VL.

Figure 5:
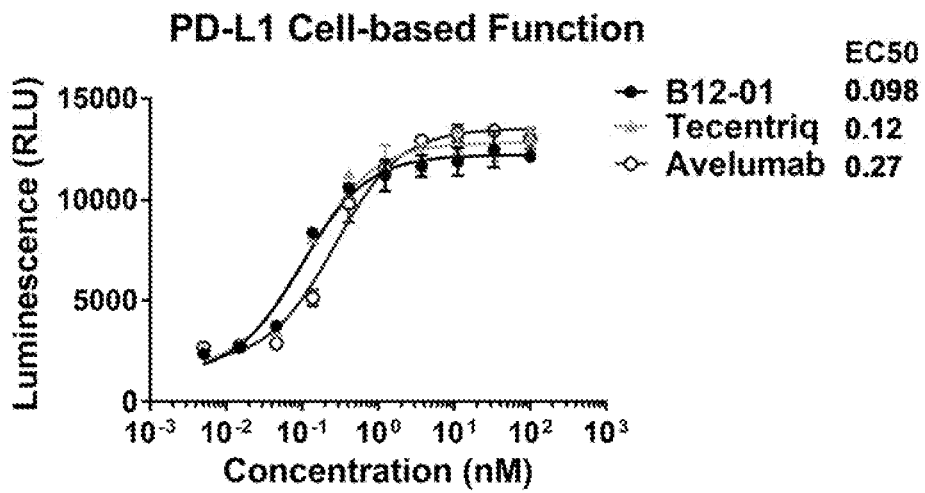
FIG. 5 presents the cell-based affinity testing results of B12-01 in comparison to Tecentriq and avelumab.

As shown in Example 5, in a cell-based affinity assay, B12-01 outperformed both atezolizumab and avelumab (FIG. 5). That B12-01 is more potent than atezolizumab is surprising because even avelumab, which was developed later than atezolizumab, was known (and hereby proven) to be less potent than atezolizumab.

Also in Example 5, in a developability assay, B12-01 exhibited higher hydrophilicity than atezolizumab, suggesting that B12-01 has higher water solubility. Such a characteristic of B12-01, therefore, gives rise to higher flexibility during formulation development. Still further, as shown in Example 7, B12-01 has cross species reactivity to cyno PD-L1 which is advantageous during preclinical studies in animal models.

In accordance with one embodiment of the present disclosure, therefore, provided is an antibodies that includes CDR regions from these newly identified antibodies. Such CDR sequences are listed in Table A below.

TABLE A

CDR sequence from antibodies B01-B17 (Kabat)

|  | HCDR1 | SEQ ID NO: | HCDR2 | SEQ ID NO: | HCDR3 | SEQ ID NO: |
|---|---|---|---|---|---|---|
| B01 | SHWLA | 35 | SIHQDASLEFYVDSVEG | 43 | GDNQFDN | 52 |
| B02 | TYIIN | 36 | SVAASGDYAYYANSVKG | 44 | DRSSGYYLSPNDAFDI | 53 |
| B03 | SYWMS | 37 | NIKEDGSEKYYVDSVKG | 45 | VVRFNDAFDI | 54 |
| B04 | SYWMS | 37 | NIKQDGSEKYYVDSVKG | 46 | TMLWDDAFDI | 55 |
| B05 | SYWMS | 37 | NIKQDGSEKYYVDSVKG | 46 | GGYYGDDDAFDI | 56 |
| B06 | DSWIH | 38 | WISPYGGSTYYADSVKG | 47 | RHWPGGFDY | 57 |
| B07 | SYWMS | 37 | NIKQDGSEKYYVDSVKG | 46 | VCGYDDAFDI | 58 |
| B08 | DHYMD | 39 | SISSSSSYIYYADSVKG | 48 | GRVGATNRFGMDV | 59 |
| B09 | SYWMS | 37 | NIKQDGSEKYYVDSVKG | 46 | EDFWSGYQDV | 60 |

TABLE A-continued

CDR sequence from antibodies B01-B17 (Kabat)

| | | | | | | | |
|---|---|---|---|---|---|---|---|
| B10 | SYWMS | 37 | NIKQDGSEKYYVDSVKG | 46 | ATVKYGGDDAFDI | 61 | |
| B11 | SYAIS | 40 | GIIPIFGTANYAQKFQG | 49 | RTDSYGYSDAFDI | 62 | |
| B12 | SYWMS | 37 | NIKQDGSEKYYVDSVKG | 46 | VALWDDAFDI | 63 | |
| B13 | SYWMS | 37 | NIKQDGSEKYYVDSVKG | 46 | STVKYGADDAFDI | 64 | |
| B14 | SYWMS | 37 | NIKEDGSEKYYVDSVKG | 45 | VVRFNDAFDI | 54 | |
| B15 | VYYMA | 41 | YTSNGDGDITYYADSVKD | 50 | AARSGYYNDY | 65 | |
| B16 | SYWMS | 37 | NIKQDGSEKYYVDSVKG | 46 | VALWDDAFDI | 63 | |
| B17 | SNAMS | 42 | AVGGGGVNTYYADSVKG | 51 | GEKGYSNSCIDY | 66 | |

| | LCDR1 | SEQ ID NO: | LCDR2 | SEQ ID NO: | LCDR3 | SEQ ID NO: |
|---|---|---|---|---|---|---|
| B01 | RASQSISSYLN | 67 | AASSLQS | 80 | QQSYSTPPT | 89 |
| B02 | RASQTISRYLN | 68 | ATSSLQS | 81 | QQSYSTPTT | 90 |
| B03 | RASQSIDTWLA | 69 | NASTLKS | 82 | QQSYSTPLT | 91 |
| B04 | RASESISSWLA | 70 | KASSLES | 83 | QQSYSTPPT | 89 |
| B05 | RASQSISSWLA | 71 | KASSLES | 83 | QQTYSLPLT | 92 |
| B06 | RASQGISSYLA | 72 | AASTLQS | 84 | QQYLSVPYT | 93 |
| B07 | RASQSISTWLA | 73 | KASSLES | 83 | QQSYSIPLT | 94 |
| B08 | RASESISRWLA | 74 | AASNLES | 85 | QQAESFPS | 95 |
| B09 | RASQSISSYLN | 67 | AASSLQS | 80 | QQSYSTPLT | 91 |
| B10 | RASQSISDWLA | 75 | KASSLES | 83 | QQSFSTPFT | 96 |
| B11 | RASQSISSYLN | 67 | AASSLQS | 80 | QQSYSTPLT | 91 |
| B12 | RASRGISSWLA | 76 | KASSLES | 83 | QQSSSIPLT | 97 |
| B13 | RASQSISSWLA | 71 | KASSLQS | 86 | QQSYSTPFT | 98 |
| B14 | RASQGISSWLA | 77 | AASSLQS | 80 | QQANSFPFT | 99 |
| B15 | RASQFISKYVN | 78 | GASILET | 87 | QQTHSTPRGV | 100 |
| B16 | RASQSISSWLA | 71 | KASSLES | 83 | QHSNSLPLT | 101 |
| B17 | QASQDISNYLN | 79 | DASNLET | 88 | QQYDNLPPFT | 102 |

It is contemplated that small changes (e.g., one amino acid addition, deletion or substitution) can be designed among these CDR sequences that can retain the antibodies' activities or even improve them. Such modified CDR sequences are referred to as CDR variants.

As demonstrated in Example 4, mutant antibodies with all of the tested CDR variants exhibited activities comparable the original antibodies. Thus, these CDR variants are within the scope of the present disclosure as well. In some embodiments, the variants have one or more of the substitutions such as D>E, S>A, G>A, N>Q, DS>ES, DS>DA, DG>DA, NS>NA, or NS>QS. Some examples are provided below.

TABLE B

Representative CDR Variants

| HCDR1 | Sequence | SEQ ID NO: |
|---|---|---|
| Original | DSWIH | 38 |
| Variants | ESWIH | 132 |

| HCDR2 | Sequence | SEQ ID NO: |
|---|---|---|
| Original | WISPYGGSTYYADSVKG | 47 |
| Variants | WISPYGGSTYYADAVKG | 133 |
| | WISPYGGSTYYAESVKG | 134 |

| HCDR2 | Sequence | SEQ ID NO: |
|---|---|---|
| Original | NIKQDGSEKYYVDSVKG | 46 |
| Variants | NIKQDGSEKYYVESVKG | 135 |
| | NIKQDASEKYYVDSVKG | 136 |
| | NIKQDASEKYYVESVKG | 137 |
| | NIKQEGSEKYYVDSVKG | 143 |
| | NIKQEGSEKYYVDAVKG | 144 |

| LCDR3 | Sequence | SEQ ID NO: |
|---|---|---|
| Original | QHSNSLPLT | 101 |
| Variants | QHSNALPLT | 138 |
| | QHSQSLPLT | 139 |

In one embodiment, the anti-PD-L1 antibody or fragment thereof includes a VH CDR1 comprising an amino acid sequence selected from SEQ ID NO:35-42 and variants thereof having one or more amino acid substitution therefrom (e.g., SEQ ID NO:132), a VH CDR2 comprising an amino acid sequence selected from SEQ ID NO:43-51 and variants thereof having one or more amino acid substitution therefrom (e.g., SEQ ID NO:133-137 and 143-144), a VH CDR3 comprising an amino acid sequence selected from SEQ ID NO:52-66 and variants thereof having one or more amino acid substitution therefrom, a VL CDR1 comprising an amino acid sequence selected from SEQ ID NO:67-79 and variants thereof having one or more amino acid substitution therefrom, a VL CDR2 comprising an amino acid sequence selected from SEQ ID NO:80-88 and variants thereof having one or more amino acid substitution therefrom, and a VL CDR3 comprising an amino acid sequence selected from SEQ ID NO:89-102 and variants thereof having one or more amino acid substitution therefrom (e.g., SEQ ID NO:138-139).

In some embodiments, the VH CDR1 comprises an amino acid sequence selected from SEQ ID NO:35-42 (or a variant such as SEQ ID NO:132), the VH CDR2 comprises an amino acid sequence selected from SEQ ID NO:43-51 (or a variant such as SEQ ID NO:133-137 and 143-144), the VH CDR3 comprises an amino acid sequence selected from SEQ ID NO:52-66, the VL CDR1 comprises an amino acid sequence selected from SEQ ID NO:67-79, the VL CDR2 comprises an amino acid sequence selected from SEQ ID NO:80-88, and the VL CDR3 comprises an amino acid sequence selected from SEQ ID NO:89-102 (or a variant such as SEQ ID NO:138-139).

In some embodiments, the CDR sequences are selected from B04, B05, B06, B07, B10, B11, B12, B13, B14 or B16. In some embodiments, the VH CDR1 comprises an amino acid sequence selected from SEQ ID NO:37-38 and 40 (or a variant such as SEQ ID NO:132), the VH CDR2 comprises an amino acid sequence selected from SEQ ID NO:45-47 and 49 (or a variant such as SEQ ID NO:133-137 and 143-144), the VH CDR3 comprises an amino acid sequence selected from SEQ ID NO:54-58 and 61-64, the VL CDR1 comprises an amino acid sequence selected from SEQ ID NO:67, 70-73 and 75-77, the VL CDR2 comprises an amino acid sequence selected from SEQ ID NO:80, 83-84 and 86, and the $V_L$ CDR3 comprises an amino acid sequence selected from SEQ ID NO:89, 91-94, 96-99 and 101 (or a variant such as SEQ ID NO:138-139).

In some embodiments, the CDR sequences are selected from B06, B12 or B16. In some embodiments, the VH CDR1 comprises an amino acid sequence selected from SEQ ID NO:37-38 (or a variant such as SEQ ID NO:132), the VH CDR2 comprises an amino acid sequence selected from SEQ ID NO:46-47 (or a variant such as SEQ ID NO:133-137 and 143-144), the VH CDR3 comprises an amino acid sequence selected from SEQ ID NO:57 and 63, the VL CDR1 comprises an amino acid sequence selected from SEQ ID NO:71-72 and 76, the VL CDR2 comprises an amino acid sequence selected from SEQ ID NO:83-84, and the VL CDR3 comprises an amino acid sequence selected from SEQ ID NO:93, 97 and 101 (or a variant such as SEQ ID NO:138-139).

The CDR sequences of an antibody or fragment of the present disclosure can be selected from a particular antibody of B01-B17, as listed in Table A. For instance, the VH CDR1 can be SEQ ID NO:35, the VH CDR2 can be SEQ ID NO:45, the VH CDR3 can be SEQ ID NO:55, the VL CDR1 can be SEQ ID NO:70, the VL CDR2 can be SEQ ID NO:83, and the VL CDR3 can be SEQ ID NO:92 (e.g., B01). A representative antibody or fragment includes a VH of SEQ ID NO:1 and a VL of SEQ ID NO:2. Other CDR sequences and VH/VL sequences are provided in Table A and Table 1.

In one embodiment, the VH CDR1 comprises the amino acid sequence of SEQ ID NO:38 (or a variant such as SEQ ID NO:132), the VH CDR2 comprises the amino acid sequence of SEQ ID NO:47 (or a variant such as SEQ ID NO:133-134), the VH CDR3 comprises the amino acid sequence of SEQ ID NO:57, the VL CDR1 comprises the amino acid sequence of SEQ ID NO:72, the VL CDR2 comprises the amino acid sequence of SEQ ID NO:84, and the VL CDR3 comprises the amino acid sequence of SEQ ID NO:93 (e.g., B06). A representative antibody or fragment includes a VH of SEQ ID NO:11 (or a variant such as SEQ ID NO:121-123) and a VL of SEQ ID NO:12.

In one embodiment, the VH CDR1 comprises the amino acid sequence of SEQ ID NO:37, the VH CDR2 comprises the amino acid sequence of SEQ ID NO:46 (or a variant such as SEQ ID NO:135-137 or 143-144), the VH CDR3 comprises the amino acid sequence of SEQ ID NO:63, the VL CDR1 comprises the amino acid sequence of SEQ ID NO:76, the VL CDR2 comprises the amino acid sequence of SEQ ID NO:83, and the VL CDR3 comprises the amino acid sequence of SEQ ID NO:97 (e.g., B12). A representative antibody or fragment includes a VH of SEQ ID NO:23 (or a variant such as SEQ ID NO:124, 126, 127, 128, 130, 140, or 145) and a VL of SEQ ID NO:24 (or a variant such as SEQ ID NO:125).

One embodiment of the present disclosure provides an antibody or antigen-binding fragment thereof, wherein the antibody or fragment thereof has specificity to a human Programmed death-ligand 1 (PD-L1) protein and comprises a heavy chain variable region (VH) comprising a VH CDR1, a VH CDR2, and a VH CDR3, and a light chain variable region (VL) comprising a VL CDR1, a VL CDR2, and a VL CDR3, wherein the VH CDR1 comprises the amino acid sequence of SEQ ID NO:37, the VH CDR2 comprises the amino acid sequence of SEQ ID NO:46, the VH CDR3 comprises the amino acid sequence of SEQ ID NO:63, the VL CDR1 comprises the amino acid sequence of SEQ ID NO:76, the VL CDR2 comprises the amino acid sequence of SEQ ID NO:83, and the VL CDR3 comprises the amino acid sequence of SEQ ID NO:97.

In some embodiments, the VH comprises the amino acid sequence of SEQ ID NO:124 or a first amino acid sequence having at least 95% (or at least 90%, 85%) sequence identity to SEQ ID NO:124, and the VL comprises the amino acid sequence of SEQ ID NO: 125 or a second amino acid sequence having at least 95% (or at least 90%, 85%) sequence identity to SEQ ID NO:125.

In one embodiment, the VH CDR1 comprises the amino acid sequence of SEQ ID NO:37, the VH CDR2 comprises the amino acid sequence of SEQ ID NO:46 (or a variant such as SEQ ID NO:135-137 or 143-144), the VH CDR3 comprises the amino acid sequence of SEQ ID NO:63, the VL CDR1 comprises the amino acid sequence of SEQ ID NO:71, the VL CDR2 comprises the amino acid sequence of SEQ ID NO:83, and the VL CDR3 comprises the amino acid sequence of SEQ ID NO:101 (or a variant such as SEQ ID NO:138-139) (e.g., B16). A representative antibody or fragment includes a VH of SEQ ID NO:31 (or a variant such as SEQ ID NO:124, 126, 127, 128, 130, 140, or 145) and a VL of SEQ ID NO:32 (or a variant such as SEQ ID NO:129 and 131).

Table A provides the CDR sequences according to the Kabat system. The Chothia system typically has different sequences for the VH CDR1 and CDR2. They are shown in Table C below.

TABLE C

CDR Sequences According to Chothia System and Variants

| | HCDR1 | SEQ ID NO: | HCDR2 | SEQ ID NO: | HCDR3 | SEQ ID NO: |
|---|---|---|---|---|---|---|
| B01 | GFTLSSH | 103 | HQDASL | 112 | GDNQFDN | 52 |
| B02 | GFTFSTY | 104 | AASGDY | 113 | DRSSGYYLSPNDAFDI | 53 |
| B03 | GFSFSSY | 105 | KEDGSE | 114 | VVRFNDAFDI | 54 |
| B04 | GFTFSSY | 106 | KQDGSE | 115 | TMLWDDAFDI | 55 |
| B05 | GFTFSSY | 106 | KQDGSE | 115 | GGYYGDDDAFDI | 56 |
| B06 | GFTFSDS | 107 | SPYGGS | 116 | RHWPGGFDY | 57 |
| B07 | GFTFSSY | 106 | KQDGSE | 115 | VCGYDDAFDI | 58 |
| B08 | GFTFSDH | 108 | SSSSSY | 117 | GRVGATNRFGMDV | 59 |
| B09 | GFTFSSY | 106 | KQDGSE | 115 | EDFWSGYQDV | 60 |
| B10 | GFTFSSY | 106 | KQDGSE | 115 | ATVKYGDDAFDI | 61 |
| B11 | GGTFSSY | 109 | IPIFGT | 118 | RTDSYGYSDAFDI | 62 |
| B12 | GFTFSSY | 106 | KQDGSE | 115 | VALWDDAFDI | 63 |
| B13 | GFTFSSY | 106 | KQDGSE | 115 | STVKYGADDAFDI | 64 |

TABLE C-continued

CDR Sequences According to Chothia System and Variants

|     |         |     |         |     |              |     |
|-----|---------|-----|---------|-----|--------------|-----|
| B14 | GFSFSSY | 105 | KEDGSE  | 114 | VVRFNDAFDI   | 54  |
| B15 | GFTFSVY | 110 | SNGDGDI | 119 | AARSGYYNDY   | 65  |
| B16 | GFTFSSY | 106 | KQDGSE  | 115 | VALWDDAFDI   | 63  |
| B17 | GFTFSSN | 111 | GGGGVN  | 120 | GEKGYSNSCIDY | 66  |

| | LCDR1 | SEQ ID NO: | LCDR2 | SEQ ID NO: | LCDR3 | SEQ ID NO: |
|---|---|---|---|---|---|---|
| B01 | RASQSISSYLN | 67 | AASSLQS | 80 | QQSYSTPPT | 89 |
| B02 | RASQTISRYLN | 68 | ATSSLQS | 81 | QQSYSTPTT | 90 |
| B03 | RASQSIDTWLA | 69 | NASTLKS | 82 | QQSYSTPLT | 91 |
| B04 | RASESISSWLA | 70 | KASSLES | 83 | QQSYSTPPT | 89 |
| B05 | RASQSISSWLA | 71 | KASSLES | 83 | QQTYSLPLT | 92 |
| B06 | RASQGISSYLA | 72 | AASTLQS | 84 | QQYLSVPYT | 93 |
| B07 | RASQSISTWLA | 73 | KASSLES | 83 | QQSYSIPLT | 94 |
| B08 | RASESISRWLA | 74 | AASNLES | 85 | QQAESFPS | 95 |
| B09 | RASQSISSYLN | 67 | AASSLQS | 80 | QQSYSTPLT | 91 |
| B10 | RASQSISDWLA | 75 | KASSLES | 83 | QQSFSTPFT | 96 |
| B11 | RASQSISSYLN | 67 | AASSLQS | 80 | QQSYSTPLT | 91 |
| B12 | RASRGISSWLA | 76 | KASSLES | 83 | QQSSSIPLT | 97 |
| B13 | RASQSISSWLA | 71 | KASSLQS | 86 | QQSYSTPFT | 98 |
| B14 | RASQGISSWLA | 77 | AASSLQS | 80 | QQANSFPFT | 99 |
| B15 | RASQFISKYVN | 78 | GASILET | 87 | QQTHSTPRGV | 100 |
| B16 | RASQSISSWLA | 71 | KASSLES | 83 | QHSNSLPLT | 101 |
| B17 | QASQDISNYLN | 79 | DASNLET | 88 | QQYDNLPPFT | 102 |

| | HCDR1 | Sequence | SEQ ID NO: |
|---|---|---|---|
| | Original | GFTFSDS | 107 |
| | Variants | GFTFSES | 141 |

| | HCDR2 | Sequence | SEQ ID NO: |
|---|---|---|---|
| | Original | KQDGSE | 115 |
| | Variants | KQDASE | 142 |

| | LCDR3 | Sequence | SEQ ID NO: |
|---|---|---|---|
| | Original | QHSNSLPLT | 101 |
| | Variants | QHSNALPLT | 138 |
| |          | QHSQSLPLT | 139 |

In one embodiment, the anti-PD-L1 antibody or fragment thereof includes a VH CDR1 comprising an amino acid sequence selected from SEQ ID NO:103-111 and variants thereof having one or more amino acid substitution therefrom (e.g., SEQ ID NO:141), a VH CDR2 comprising an amino acid sequence selected from SEQ ID NO:112-120 and variants thereof having one or more amino acid substitution therefrom (e.g., SEQ ID NO:142), a VH CDR3 comprising an amino acid sequence selected from SEQ ID NO:52-66 and variants thereof having one or more amino acid substitution therefrom, a VL CDR1 comprising an amino acid sequence selected from SEQ ID NO:67-79 and variants thereof having one or more amino acid substitution therefrom, a VL CDR2 comprising an amino acid sequence selected from SEQ ID NO:80-88 and variants thereof having one or more amino acid substitution therefrom, and a VL CDR3 comprising an amino acid sequence selected from SEQ ID NO:89-102 and variants thereof having one or more amino acid substitution therefrom (e.g., SEQ ID NO:138-139).

In some embodiments, the VH CDR1 comprises an amino acid sequence selected from SEQ ID NO: 103-111 (or a variant such as SEQ ID NO:141), the VH CDR2 comprises an amino acid sequence selected from SEQ ID NO: 112-120 (or a variant such as SEQ ID NO:142), the VH CDR3 comprises an amino acid sequence selected from SEQ ID NO:52-66, the VL CDR1 comprises an amino acid sequence selected from SEQ ID NO:67-79, the VL CDR2 comprises an amino acid sequence selected from SEQ ID NO:80-88, and the VL CDR3 comprises an amino acid sequence selected from SEQ ID NO:89-102 (or a variant such as SEQ ID NO:138-139).

In some embodiments, the CDR sequences are selected from B04, B05, B06, B07, B10, B11, B12, B13, B14 or B16. In some embodiments, the VH CDR1 comprises an amino acid sequence selected from SEQ ID NO:105-107 and 109 (or a variant such as SEQ ID NO:141), the VH CDR2 comprises an amino acid sequence selected from SEQ ID NO:114-116 and 118 (or a variant such as SEQ ID NO:142), the VH CDR3 comprises an amino acid sequence selected from SEQ ID NO:54-58 and 61-64, the VL CDR1 comprises an amino acid sequence selected from SEQ ID NO:67, 70-73 and 75-77, the VL CDR2 comprises an amino acid sequence selected from SEQ ID NO:80, 83-84 and 86, and the VL CDR3 comprises an amino acid sequence selected from SEQ ID NO:89, 91-94, 96-99 and 101 (or a variant such as SEQ ID NO:138-139).

In some embodiments, the CDR sequences are selected from B06, B12 or B16. In some embodiments, the VH CDR1 comprises an amino acid sequence selected from SEQ ID NO:106-107 (or a variant such as SEQ ID NO:141), the VH CDR2 comprises an amino acid sequence selected from SEQ ID NO:115-116 (or a variant such as SEQ ID NO:142), the VH CDR3 comprises an amino acid sequence selected from SEQ ID NO:57 and 63, the VL CDR1 comprises an amino acid sequence selected from SEQ ID NO:71-72 and 76, the VL CDR2 comprises an amino acid sequence selected from SEQ ID NO:83-84, and the VL CDR3 comprises an amino acid sequence selected from SEQ ID NO:93, 97 and 101 (or a variant such as SEQ ID NO:138-139).

The CDR sequences of an antibody or fragment of the present disclosure can be selected from a particular antibody of B01-B17, as listed in Table A. For instance, the VH CDR1 can be SEQ ID NO:35, the VH CDR2 can be SEQ ID NO:45, the VH CDR3 can be SEQ ID NO:55, the VL CDR1 can be SEQ ID NO:70, the VL CDR2 can be SEQ ID NO:83, and the VL CDR3 can be SEQ ID NO:92 (e.g., B01). A representative antibody or fragment includes a VH of SEQ ID NO:1 and a VL of SEQ ID NO:2. Other CDR sequences and VH/VL sequences are provided in Table A and Table 1.

In one embodiment, the VH CDR1 comprises the amino acid sequence of SEQ ID NO:107 (or a variant such as SEQ ID NO:141), the VH CDR2 comprises the amino acid sequence of SEQ ID NO:116, the VH CDR3 comprises the amino acid sequence of SEQ ID NO:57, the VL CDR1 comprises the amino acid sequence of SEQ ID NO:72, the VL CDR2 comprises the amino acid sequence of SEQ ID NO:84, and the VL CDR3 comprises the amino acid sequence of SEQ ID NO:93 (e.g., B06). A representative antibody or fragment includes a VH of SEQ ID NO:11 (or a variant such as SEQ ID NO:121-123) and a VL of SEQ ID NO:12.

In one embodiment, the VH CDR1 comprises the amino acid sequence of SEQ ID NO:106, the VH CDR2 comprises the amino acid sequence of SEQ ID NO:115 (or a variant such as SEQ ID NO:142), the VH CDR3 comprises the amino acid sequence of SEQ ID NO:63, the VL CDR1 comprises the amino acid sequence of SEQ ID NO:76, the VL CDR2 comprises the amino acid sequence of SEQ ID NO:83, and the VL CDR3 comprises the amino acid sequence of SEQ ID NO:97 (e.g., B12). A representative antibody or fragment includes a VH of SEQ ID NO:23 (or a variant such as SEQ ID NO:124, 126, 127, 128, 130, 140, or 145) and a VL of SEQ ID NO:24 (or a variant such as SEQ ID NO:125).

In one embodiment, the VH CDR1 comprises the amino acid sequence of SEQ ID NO:106, the VH CDR2 comprises the amino acid sequence of SEQ ID NO:115 (or a variant such as SEQ ID NO:142), the VH CDR3 comprises the amino acid sequence of SEQ ID NO:63, the VL CDR1 comprises the amino acid sequence of SEQ ID NO:71, the VL CDR2 comprises the amino acid sequence of SEQ ID NO:83, and the VL CDR3 comprises the amino acid sequence of SEQ ID NO:101 (or a variant such as SEQ ID NO:138-139) (e.g., B16). A representative antibody or fragment includes a VH of SEQ ID NO:31 (or a variant such as SEQ ID NO:124, 126, 127, 128, 130, 140, or 145) and a VL of SEQ ID NO:32 (or a variant such as SEQ ID NO:129 and 131).

Also provided, in some embodiments, are anti-PD-L1 antibodies and antigen binding fragments that compete with any of the antibodies disclosed herein in binding to human PD-L1. Also provided, in some embodiments, are anti-PD-L1 antibodies and antigen binding fragments that bind to the same epitope as any of the antibodies disclosed herein. Also provided, in some embodiments, are anti-PD-L1 antibodies and antigen binding fragments that included the VH CDR1, CDR2, and CDR3 and VL CDR1, CDR2 and CDR3 of the antibodies disclosed herein.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence. In some embodiments, the modified antibody or fragment retains the designate CDR sequences.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Cancer Treatment

As described herein, the antibodies, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies of the disclosure can also be used to treat or inhibit cancer. PD-L1 can be overexpressed in tumor cells. Tumor-derived PD-L1 can bind to PD-1 on immune cells thereby limiting antitumor T-cell immunity. Results with small molecule inhibitors, or monoclonal antibodies targeting PD-L1 in murine tumor models, indicate that targeted PD-L1 therapy is an important alternative and realistic approach to effective control of tumor growth. As demonstrated in the experimental examples, the anti-PD-L1 antibodies activated the adaptive immune response machinery, which can lead to improved survival in cancer patients.

Accordingly, in some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient expresses, over-express, or is induced to express PD-L1. Induction of PD-L1 expression, for instance, can be done by administration of a tumor vaccine or radiotherapy.

Tumors that express the PD-L1 protein include those of bladder cancer, non-small cell lung cancer, renal cancer, breast cancer, urethral cancer, colorectal cancer, head and neck cancer, squamous cell cancer, Merkel cell carcinoma, gastrointestinal cancer, stomach cancer, oesophageal cancer, ovarian cancer, renal cancer, and small cell lung cancer. Accordingly, the presently disclosed antibodies can be used for treating any one or more such cancers.

Cellular therapies, such as chimeric antigen receptor (CAR) T-cell therapies, are also provided in the present disclosure. A suitable cell can be used, that is put in contact with an anti-PD-L1 antibody of the present disclosure (or alternatively engineered to express an anti-PD-L1 antibody of the present disclosure). Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, thyroid cancer, endometrial cancer, melanoma, prostate cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Treatment of Infections

As demonstrated in the experimental examples, the antibodies of the present disclosure can activate immune response which can then be useful for treating infections.

Infection is the invasion of an organism's body tissues by disease-causing agents, their multiplication, and the reaction of host tissues to these organisms and the toxins they produce. An infection can be caused by infectious agents such as viruses, viroids, prions, bacteria, nematodes such as parasitic roundworms and pinworms, arthropods such as ticks, mites, fleas, and lice, fungi such as ringworm, and other macroparasites such as tapeworms and other helminths. In one aspect, the infectious agent is a bacterium, such as Gram negative bacterium. In one aspect, the infectious agent is virus, such as DNA viruses, RNA viruses, and reverse transcribing viruses. Non-limiting examples of viruses include Adenovirus, Coxsackievirus, Epstein-Barr virus, Hepatitis A virus, Hepatitis B virus, Hepatitis C virus, Herpes simplex virus, type 1, Herpes simplex virus, type 2, Cytomegalovirus, Human herpesvirus, type 8, HIV, Influenza virus, Measles virus, Mumps virus, Human papillomavirus, Parainfluenza virus, Poliovirus, Rabies virus, Respiratory syncytial virus, Rubella virus, Varicella-zoster virus.

The antibodies of the present disclosure can also be used to treat an infectious disease caused by a microorganism, or kill a microorganism, by targeting the microorganism and an immune cell to effect elimination of the microorganism. In one aspect, the microorganism is a virus including RNA and DNA viruses, a Gram positive bacterium, a Gram negative bacterium, a protozoa or a fungus.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracistemally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antibodies polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

The methods for treating an infectious or malignant disease, condition or disorder comprising administration of an antibody, variant, or derivative thereof of the disclosure are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of antigen-binding polypeptide described herein include the effect of an antigen-binding polypeptide on a cell line or a patient tissue sample. The effect of the antigen-binding polypeptide on the cell line and/or tissue sample can be determined utilizing techniques known to those of skill in the art, such as the assays disclosed elsewhere herein. In accordance with the disclosure, in vitro assays which can be used to determine whether administration of a specific antigen-binding polypeptide is indicated, include in vitro cell culture assays in which a patient tissue sample is grown in culture, and exposed to or otherwise administered a compound, and the effect of such compound upon the tissue sample is observed.

Diagnostic Methods

Over-expression of PD-L1 is observed in certain tumor samples, and patients having PD-L1-over-expressing cells are likely responsive to treatments with the anti-PD-L1 antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with a PD-L1 protein potentially present in the sample. Methods such as ELISA can be used, taking advantage of the anti-PD-L1 antibody, to detect the presence of the PD-L1 protein in the sample.

Presence of the PD-L1 protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

EXAMPLES

Example 1: Full Human Naïve Phage Library Panning and Screening

This example shows the screening of full human anti-PD-L1 antibodies from a phage library.

Antigen: human PDL1 extracellular domain (ECD) avi-His-biotion labeled protein (B3568B, Biointron).

Preparation of full human naïve phage library: The phage library was constructed by using phagemid vectors which consisted of antibody gene fragments that were amplified from PBMCs of healthy human subjects. It was constructed as a Fab phage library. The library size was $2\times10^{11}$.

Phage library solution panning against PDL1 ECD protein. The phage libraries first underwent negative screening by incubating with BSA-coated streptavidin Dynabeads. The resulting phages were incubated with PDL1-ECD-avi-his-biotin protein and washed by Kingfihser magnetic beads system. The binders were eluted by trypsin. The eluted phages (output 1) were subsequently tested for their titer to bind antigen and co-cultured with *E. coli*. There were three rounds of panning and screening. The titers of output 2 and output 3 were significantly increased.

Single clones were cherrypicked from output 2 and 3 and then cultured in 96 deep well plate. The culture supernatant was subject to IgG concentration and antigen binding titer evaluation. 277 positive clones were selected and subject to sequencing. Post sequence analysis 128 unique sequences were identified. All these clones were subjected to ELISA binding analysis. 17 top sequences were identified see below table. 17 top binding sequences were identified see Table 1 below.

TABLE 1

Candidate antibody sequences

| Clone | AA sequence (SEQ ID NO:) (CDRs according to Kabat system are underlined) | Antibody No. |
|---|---|---|
| 67A3-5 | VH (SEQ ID NO: 1) EVQLLESGGGLVQPGGSLRLSCAASGFTLSSHWLAWVRQAPGKGLEWVASIHQDASLEFYVDSVEGRFTISRDNSKRSLFLQMNNLRVEDTAVYYCARGDNQFDNWGQGTLVTVSA<br>VL (SEQ ID NO: 2) DIVMTQSPSSLSASVGDRVTITCRASQSISSYLNWYQQKPGKAPKLLIYAASSLQSGVPSRFSGSGSGTDFTLTISSLQPEDFATYYCQQSYSTPPTFGPGTKVDIK | B01 |
| 67A2-20 | VH (SEQ ID NO: 3) QVQLLESGGGLVKPGGSLRLSCAASGFTFSTYIINWVRQAPGKGLEWVSSVAASGDYAYYANSVKGRFTISRDNSKNTLYLQMNSLRAEDTAVYYCARDRSSGYYLSPNDAFDIWGQGTMVTVSA<br>VL (SEQ ID NO: 4) NIQLTQSPSSLSASLGDRVTITCRASQTISRYLNWYQQKPGKAPELLIYATSSLQSGVPSRFSGSGSGTDFTLTISSLQPEDFATYYCQQSYSTPTTFGGGTKVEIK | B02 |
| 67A3-14 | VH (SEQ ID NO: 5) EVQLLESGGGLVQPGGSLRLSCAASGFSFSSYWMSWVRQAPGKGLEWVANIKEDGSEKYYVDSVKGRFTISRDNAKNSLYLQMNSLRAEDTAVYYCARVVRFNDAFDIWGQGTMVTVSA<br>VL (SEQ ID NO: 6) DIQLTQSPSTLSASVGDRVTITCRASQSIDTWLAWYQQKPGKAPKLLIHNASTLKSGVSSRFSGSGSGTDFTLTISSLQPEDFATYYCQQSYSTPLTFGGGTKVEIK | B03 |
| 67A3-15 | VH (SEQ ID NO: 7) QVQLLDSGGGLVQPGGSLRLSCAASGFTFSSYWMSWVRQAPGKGLEWVANIKQDGSEKYYVDSVKGRFTISRDNAKNSLYLQMNSLRAEDTAVYYCARTMLWDDAFDIWGQGTMVTVSA<br>VL (SEQ ID NO: 8) DIQLTQSPSTLSASVGDRVTITCRASESISSWLAWYQQKPGKVPKLLIYKASSLESGVPSRFSGSGSGTDFTLTISSLQPEDFATYYCQQSYSTPPTFGQGTKVEIK | B04 |
| 67A3-21 | VH (SEQ ID NO: 9) EVQLVETGRGLVQPGRSLRLSCAASGFTFSSYWMSWVRQAPGKGLEWVANIKQDGSEKYYVDSVKGRFTISRDNAKNSLYLQMNSLRAEDTAVYYCARGGYYGDDDAFDIWGQGTMVTVSA | B05 |

TABLE 1-continued

Candidate antibody sequences

| Clone | AA sequence (SEQ ID NO:) (CDRs according to Kabat system are underlined) | Antibody No. |
|---|---|---|
| | VL (SEQ ID NO: 10)<br>NIQMTQSPSTLSASVGDRVTITCRASQSISSWLAWYQQKPGKAP<br>KLLIYKASSLESGV<br>PSRFSGSGSGTEFTLTISSLQPEDFATYYCQQTYSLPLTFGQGT<br>RVGIK | |
| 67A3-40 | VH (SEQ ID NO: 11)<br>EVQLVESGGGLVQPGGSLRLSCAASGFTFSDSWIHWVRQAPGKG<br>LEWVAWISPYGGST<br>YYADSVKGRFTISADTSKNTAYLQMNSLRAEDTAVYYCARRHWP<br>GGFDYWGQGTLVTVSA<br>VL (SEQ ID NO: 12)<br>DIQMTQSPSSLSASVGDRVTITCRASQGISSYLAWYQQKPGKAP<br>KLLIYAASTLQSGV<br>PDRFSGSGSGTDFTLTISSLQAEDVAVYYCQQYLSVPYTFGQGT<br>KVEIK | B06 |
| 67C1-5 | VH (SEQ ID NO: 13)<br>EVQLLESGGGLVQPGGSLRLSCAASGFTFSSYWMSWVRQAPGKG<br>LEWVANIKQDGSEK<br>YYVDSVKGRFTISRDNAKNSLYLQMNSLRAEDTAVYYCARVCGY<br>DDAFDIWGQGTMVTVSA<br>VL (SEQ ID NO: 14)<br>NIQMTHSPSTLSASVGDRVTISCRASQSISTWLAWYQQKPGKAP<br>KLLIYKASSLESGV<br>PSRFSGSGSGTDFTLTISSLQPEDFATYYCQQSYSIPLTFGGGT<br>KVEIK | B07 |
| 67C2-1 | VH (SEQ ID NO: 15)<br>EVQLLESGGGLVQPGGSLRLSCVGSGFTFSDHYMDWVRQAPGKG<br>LEWVSSISSSSSYI<br>YYADSVKGRFTISRDNAKNSLYLQMNSLRAEDTAVYYCARGRVG<br>ATNRFGMDVWGQGTMVTVSA<br>VL (SEQ ID NO: 16)<br>DIQMIQSPSSVSASVGDRVTITCRASESISRWLAWYQQKPGKAP<br>KLLIYAASNLESGV<br>PSRFSGSGSGTEFTLTISSLQPEDFATYYCQQAESFPSFGQGTR<br>LEIK | B08 |
| 67C2-9 | VH (SEQ ID NO: 17)<br>EVQLLESGGGLVQPGGSLRLSCAASGFTFSSYWMSWVRQAPGKG<br>LEWVANIKQDGSEK<br>YYVDSVKGRFTISRDNAKNSLYLQMNSLRAEDTAVYYCAREDFW<br>SGYQDVWGQGTMVTVSA<br>VL (SEQ ID NO: 18)<br>DIQLTQSPSSLSASVGDRVTITCRASQSISSYLNWYQQKPGKAP<br>KLLIYAASSLQSGV<br>PSRFSGSGSGTDFTLTISSLQPEDFATYYCQQSYSTPLTFGGGT<br>KVEIK | B09 |
| 67C3-14 | VH (SEQ ID NO: 19)<br>QVQLVQSGGGLVQPGGSLRLSCAASGFTFSSYWMSWVRQAPGKG<br>LEWVANIKQDGSEK<br>YYVDSVKGRFTISRDNAKNSLFLQMNSLGAEDTAMYYCARATVK<br>YGGDDAFDIWGQGTMVTVSA<br>VL (SEQ ID NO: 20)<br>NIQLTQSPSTLSASVGDRVTITCRASQSISDWLAWYQQKPGKAP<br>NLLIYKASSLESGV<br>PSRFSGSGSGTDFTLTISSLQPEDFATYYCQQSFSTPFTFGPGT<br>KVDIK | B10 |
| 67C3-17 | VH (SEQ ID NO: 21)<br>EVQLLESGAEVKKPGSSVKVSCKASGGTFSSYAISWVRQAPGQG<br>LEWMGGIIPIFGTA<br>NYAQKFQGRVTITADESTSTAYMELSSLRSEDTAVYYCARRTDS<br>YGYSDAFDIWGQGTMVTVSA<br>VL (SEQ ID NO: 22)<br>DIQLTQSPSSLSASVGDRVTITCRASQSISSYLNWYQQKPGKAP<br>KLLIYAASSLQSGV<br>PSRFSGSGSGTDFTLTISSLQPEDFATYYCQQSYSTPLTFGGGT<br>KVEIK | B11 |

TABLE 1-continued

Candidate antibody sequences

| Clone | AA sequence (SEQ ID NO:) (CDRs according to Kabat system are underlined) | Antibody No. |
|---|---|---|
| 67C1-9 | VH (SEQ ID NO: 23)<br>QVQLLESGGGLVQPGGSLRLSCAASGFTFSSYWMSWVRQAPGKG<br>LEWVANIKQDGSEK<br>YYVDSVKGRFTISRDNAKNSLYLQMNSLRAEDTAVYYCARVALW<br>DDAFDIWGQGTMVTVSA<br>VL (SEQ ID NO: 24)<br>NIQLTQSPSTLSASVGDRVIITCRASRGISSWLAWYQQKPGKAP<br>NLLISKASSLESGV<br>PSRFSGSGSGTDFTLTISSLQPEDFATYYCQQSSSIPLTFGGGT<br>KVEIK | B12 |
| 67C1-10 | VH (SEQ ID NO: 25)<br>EVQLLESGGGLVQPGGSLRLSCAASGFTFSSYWMSWVRQAPGKG<br>LEWVANIKQDGSEK<br>YYVDSVKGRFTISRDNAKNSLYLQMNSLRAEDTAVYFCARSTVK<br>YGADDAFDIWGQGAMVTVSA<br>VL (SEQ ID NO: 26)<br>NIQMTQSPSTLSASVGDRVTITCRASQSISSWLAWYQQKPGKAP<br>KLLIYKASSLQSGV<br>PSRFSGSGSGTDFTLTISSLQPEDFATYYCQQSYSTPFTFGPGT<br>KVDIK | B13 |
| 67C2-19 | VH (SEQ ID NO: 27)<br>EVQLLESGGGEVQPGRSLRLSCAASGFSFSSYWMSWVRQAPGKG<br>LEWVANIKEDGSEK<br>YYVDSVKGRFTISRDNAKNSLYLQMNSLRAEDTAVYYCARVVRF<br>NDAFDIWGQGTMVTVSA<br>VL (SEQ ID NO: 28)<br>NIQLTQSPSSVSASVGDRVTITCRASQGISSWLAWYQQKPGKAP<br>KLLIYAASSLQSGV<br>PSRFSGSGSGTDFTLTISSLQPEDFATYYCQQANSFPFTFGPGT<br>KVDIK | B14 |
| 67C1-14 | VH (SEQ ID NO: 29)<br>EVQLLESGGGLVKPGGSLRLSCSASGFTFSVYYMAWIRQAPGEG<br>LEWISYTSNGDGDI<br>TYYADSVKDRFTISRDNAKNSLLLQMNSLRDEDTAVYYCVRAAR<br>SGYYNDYWGQGTLVTVSA<br>VL (SEQ ID NO: 30)<br>DIQLTQSPSSLSASVGDRVTMTCRASQFISKYVNWYQQKPGKAP<br>KVLIYGASILETGV<br>PSRFSGSGSGFGTDFTFTISSLQPEDFATYYCQQTHSTPRGVFGQG<br>TRVEVK | B15 |
| 67C3-10 | VH (SEQ ID NO: 31)<br>QVQLLDSGGGLVQPGGSLRLSCAASGFTFSSYWMSWVRQAPGKG<br>LEWVANIKQDGSEK<br>YYVDSVKGRFTISRDNAKNSLYLQMNSLRAEDTAVYYCARVALW<br>DDAFDIWGQGTMVTVSA<br>VL (SEQ ID NO: 32)<br>DIQMTQSPSSLSASVGDRVTITCRASQSISSWLAWYQQKPGKAP<br>KLLIYKASSLESGV<br>PSRFSGSGSGTEFTLTISSLQPDDFATYYCQHSNSLPLTFGGGT<br>KVEIK | B16 |
| 67C2-23 | VH (SEQ ID NO: 33)<br>EVQLLESGGGLVQPGGSLRLSCAASGFTFSSNAMSWVRQAPGKG<br>LEWVSAVGGGGVNT<br>YYADSVKGRFTISRDNSKNTLYLQMNSLRAEDTAVYYCAKGEKG<br>YSNSCIDYWGQGTLVTVSA<br>VL (SEQ ID NO: 34)<br>NIQLTQSPSSLSASVGDRVTITCQASQDISNYLNWYQQKPGKAP<br>KLLIYDASNLETGV<br>PSRFSGSGSGTDFTFTISSLQPEDIATYYCQQYDNLPPFTFGPG<br>TKVDIK | B17 |

Example 2. Binding Property Analysis of PDL1 Antibodies

The 17 unique clones were characterized and converted into full-length IgG. Their binding property was examined with recombinant human PD-L1 (Sino Biological, Cat #: 10084-H08H).

To evaluate antigen binding activity, the antibodies were subjected to ELISA test. Briefly, microtiter plates were coated with human PD-L1 protein at 1 µg/ml in PBS, 100 µl/well at 4° C. overnight, then blocked with 100 µl/well of 1% BSA. 4-fold dilutions of humanized antibodies starting from 10 µg/ml were added to each well and incubated for 1-2 hours at RT. The plates were washed with PBS/Tween and then incubate with goat-anti-human IgG antibody conjugated with Horse Radish Peroxidase (HRP) for 1 hour at RT. After washing, the plates were developed with TMB substrate and analyzed by spectrophotometer at OD 450 nm. As shown in FIG. 1, all the antibodies showed binding efficacy to human PD-L1. In particular, B03, B04, B05, B06, B07, B10, B12, B13, B14 and B16 showed excellent binding to human PD-L1. Among these binders, B04, B06, B07, B12 and B16 were comparable or better than Tecentriq® (Atezolizumab), a reference anti-PD-L1 antibody.

Example 3. Cell Based Functional Analysis of PDL1 Antibody

To test the ability of the anti-PDL1 antibodies to stimulate T cell response, hPD-1-expressed Jurkat cells were used. Jurkat is a human T cell leukemia cell line that can activate NF-AT activated luciferase expression upon TCR stimulation. In this assay, Jurkat cells transfected with human PD-1 gene by lentivirus were used as the responder cells. The Raji-PD-L1 cells was used as the antigen presenting cells (APC). Staphylococcal Enterotoxins (SE) are used to stimulate TCR signal. In this system, ectopically expressed huPDL1 can suppress SE stimulated NF-AT-luciferase activity in Jurkat cells, while anti-PDL1 antibodies can reverse NF-AT-luciferase activity.

Figure 2:
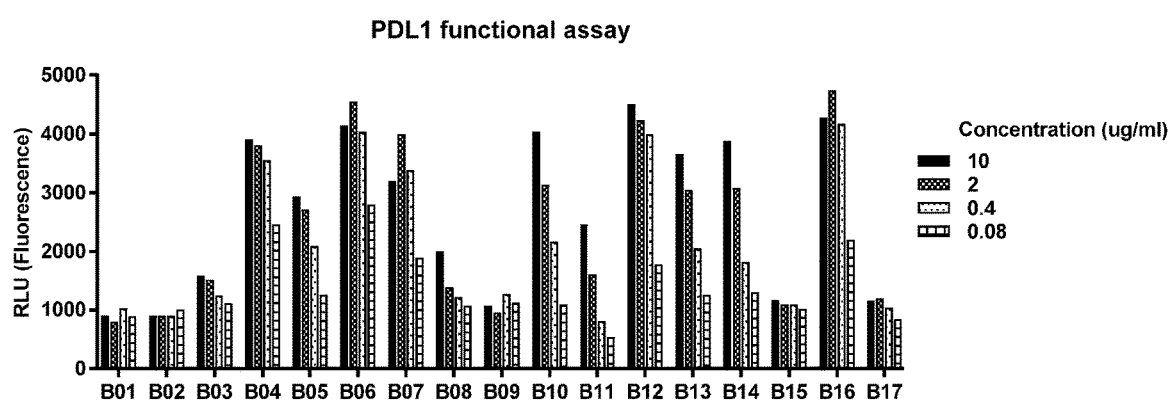
FIG. 2 shows the antibodies' activity in blocking the PD1/PDL1 mediated NF-AT-luciferase activity.

In short, APCs (2.5×10$^4$) were co-cultured with PD-1 expressing Jurkat T cells (1×10$^5$) in the presence of SE stimulation. Anti-PDL1 antibodies were added at the beginning of the culture. 6 hr later, the resulting cells were evaluated for its luciferase activity. As shown in FIG. 2, antibodies B04, B05, B06, B07, B10, B11, B12, B13, B14 and B16 dose dependently blocked the PD1/PDL1 mediated NF-AT-luciferase activity.

Figure 3:
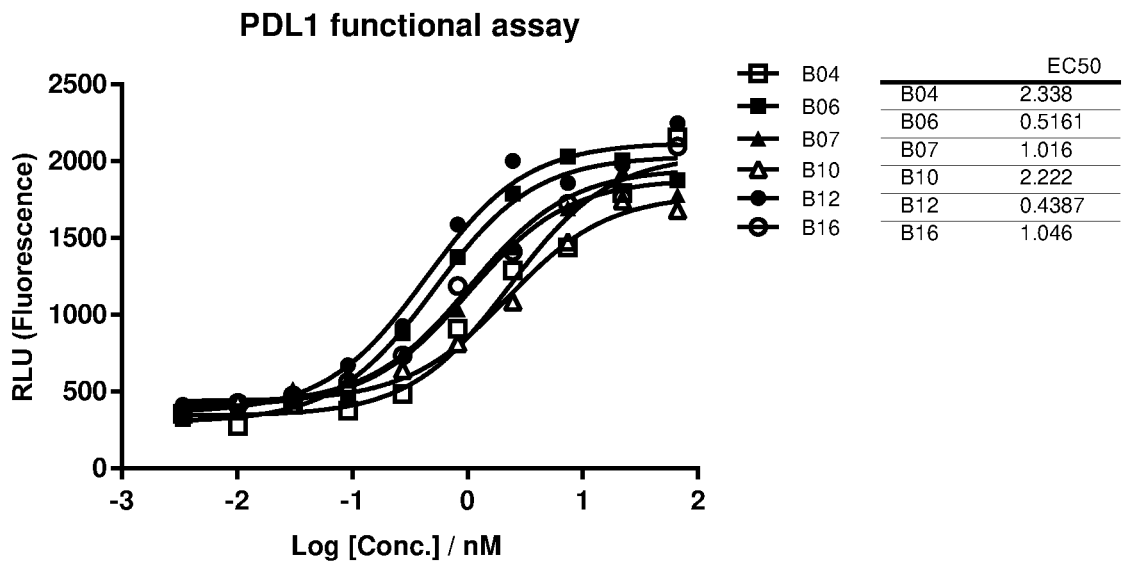
FIG. 3 shows that all tested antibodies dose-dependenity reversed PD1/PDL1 mediated NF-AT-luciferase inhibition.

To further evaluate the function of PDL1 blocking antibodies, selected antibodies (B04, B06, B07, B10, B12, B16) were further evaluated for their function in Jurkat PD1 assay with more doses. As shown in FIG. 3, all of these antibodies dose dependently reversed the PD1/PDL1 mediated NF-AT-luciferase inhibition. Among them, B06, B07, B12 and B16 were the most potent antibodies.

Example 4. Post-Translational Modification (PTM) Removing Design

There are usually post-translational modification (PTM) sites in the CDR regions of human antibody sequences. Sequence examination also found potential isomerization of aspartic acid (Asp) in DS or DG and deamidation sites in B06, B12 or B16 sites. Some of such amino acid substitutions (Table 2) were prepared and tested. The tested sequences also included certain customary changes in the framework regions for therapeutic antibodies, e.g., a serine at the C-terminus of VH and a DIQM stretch at the N-terminus of the VL.

TABLE 2

| | Mutated antibody sequences |
|---|---|
| B06 | AA sequence (mutation underlined) |
| B06-01 | VH (SEQ ID NO: 121)<br>EVQLVESGGGLVQPGGSLRLSCAASGFTFSDSWIHWVRQA<br>PGKGLEWVAWISPYGGST<br>YYADSVKGRFTISADTSKNTAYLQMNSLRAEDTAVYYCAR<br>RHWPGGFDYWGQGTLVTVS<u>S</u><br>VL (SEQ ID NO: 12)<br>DIQMTQSPSSLSASVGDRVTITCRASQGISSYLAWYQQKP<br>GKAPKLLIYAASTLQSGV<br>PDRFSGSGSGTDFTLTISSLQAEDVAVYYCQQYLSVPYTF<br>GQGTKVEIK |
| B06-02 | VH (SEQ ID NO: 122)<br>EVQLVESGGGLVQPGGSLRLSCAASGFTFS<u>E</u>SWIHWVRQA<br>PGKGLEWVAWISPYGGST<br>YYADSVKGRFTISADTSKNTAYLQMNSLRAEDTAVYYCAR<br>RHWPGGFDYWGQGTLVTVS<u>S</u><br>VL (SEQ ID NO: 12)<br>DIQMTQSPSSLSASVGDRVTITCRASQGISSYLAWYQQKP<br>GKAPKLLIYAASTLQSGV<br>PDRFSGSGSGTDFTLTISSLQAEDVAVYYCQQYLSVPYTF<br>GQGTKVEIK |
| B06-03 | VH (SEQ ID NO: 123)<br>EVQLVESGGGLVQPGGSLRLSCAASGFTFS<u>E</u>SWIHWVRQA<br>PGKGLEWVAWISPYGGST<br>YYAD<u>A</u>VKGRFTISADTSKNTAYLQMNSLRAEDTAVYYCAR<br>RHWPGGFDYWGQGTLVTVS<u>S</u><br>VL (SEQ ID NO: 12)<br>DIQMTQSPSSLSASVGDRVTITCRASQGISSYLAWYQQKP<br>GKAPKLLIYAASTLQSGV<br>PDRFSGSGSGTDFTLTISSLQAEDVAVYYCQQYLSVPYTF<br>GQGTKVEIK |
| B12 | AA sequence (mutation underlined) |
| B12-01 | VH (SEQ ID NO: 124)<br>QVQLLESGGGLVQPGGSLRLSCAASGFTFSSYWMSWVRQA<br>PGKGLEWVANIKQDGSEK<br>YYVDSVKGRFTISRDNAKNSLYLQMNSLRAEDTAVYYCAR<br>VALWDDAFDIWGQGTMVTVS<u>S</u><br>VL (SEQ ID NO: 125)<br><u>DIQM</u>TQSPSTLSASVGDRVIITCRASRGISSWLAWYQQKP<br>GKAPNLLISKASSLESGV<br>PSRFSGSGSGTDFTLTISSLQPEDFATYYCQQSSSIPLTF<br>GGGTKVEIK |
| B12-02 | VH (SEQ ID NO: 126)<br>QVQLLESGGGLVQPGGSLRLSCAASGFTFSSYWMSWVRQA<br>PGKGLEWVANIKQ<u>E</u>GSEK<br>YYVDSVKGRFTISRDNAKNSLYLQMNSLRAEDTAVYYCAR<br>VALWDDAFDIWGQGTMVTVS<u>S</u><br>VL (SEQ ID NO: 125)<br><u>DIQM</u>TQSPSTLSASVGDRVIITCRASRGISSWLAWYQQKP<br>GKAPNLLISKASSLESGV<br>PSRFSGSGSGTDFTLTISSLQPEDFATYYCQQSSSIPLTF<br>GGGTKVEIK |
| B12-02a | VH (SEQ ID NO: 128)<br>QVQLLESGGGLVQPGGSLRLSCAASGFTFSSYWMSWVRQA<br>PGKGLEWVANIKQDGSEK<br>YYV<u>E</u>SVKGRFTISRDNAKNSLYLQMNSLRAEDTAVYYCAR<br>VALWDDAFDIWGQGTMVTVS<u>S</u><br>VL (SEQ ID NO: 125)<br><u>DIQM</u>TQSPSTLSASVGDRVIITCRASRGISSWLAWYQQKP<br>GKAPNLLISKASSLESGV<br>PSRFSGSGSGTDFTLTISSLQPEDFATYYCQQSSSIPLTF<br>GGGTKVEIK |

TABLE 2-continued

Mutated antibody sequences

B12-03  
VH (SEQ ID NO: 140)  
QVQLLESGGGLVQPGGSLRLSCAASGFTFSSYWMSWVRQA
PGKGLEWVANIKQEGSEK
YYVDAVKGRFTISRDNAKNSLYLQMNSLRAEDTAVYYCAR
VALWDDAFDIWGQGTMVTVSS  
VL (SEQ ID NO: 125)  
DIQMTQSPSTLSASVGDRVIITCRASRGISSWLAWYQQKP
GKAPNLLISKASSLESGV
PSRFSGSGSGTDFTLTISSLQPEDFATYYCQQSSSIPLTF
GGGTKVEIK

B12-03a  
VH (SEQ ID NO: 127)  
QVQLLESGGGLVQPGGSLRLSCAASGFTFSSYWMSWVRQA
PGKGLEWVANIKQDASEK
YYVDSVKGRFTISRDNAKNSLYLQMNSLRAEDTAVYYCAR
VALWDDAFDIWGQGTMVTVSS  
VL (SEQ ID NO: 125)  
DIQMTQSPSTLSASVGDRVIITCRASRGISSWLAWYQQKP
GKAPNLLISKASSLESGV
PSRFSGSGSGTDFTLTISSLQPEDFATYYCQQSSSIPLTF
GGGTKVEIK

B16 AA sequence (mutation underlined)

B16-01  
VH (SEQ ID NO: 145)  
QVQLLDSGGGLVQPGGSLRLSCAASGFTFSSYWMSWVRQA
PGKGLEWVANIKQDGSEK
YYVDSVKGRFTISRDNAKNSLYLQMNSLRAEDTAVYYCAR
VALWDDAFDIWGQGTMVTVSS  
VL (SEQ ID NO: 32)  
DIQMTQSPSSLSASVGDRVTITCRASQSISSWLAWYQQKP
GKAPKLLIYKASSLESGV
PSRFSGSGSGTEFTLTISSLQPDDFATYYCQHSNSLPLTF
GGGTKVEIK

B16-01a  
VH (SEQ ID NO: 124)  
QVQLLESGGGLVQPGGSLRLSCAASGFTFSSYWMSWVRQA
PGKGLEWVANIKQDGSEK
YYVDSVKGRFTISRDNAKNSLYLQMNSLRAEDTAVYYCAR
VALWDDAFDIWGQGTMVTVSS  
VL (SEQ ID NO: 32)  
DIQMTQSPSSLSASVGDRVTITCRASQSISSWLAWYQQKP
GKAPKLLIYKASSLESGV
PSRFSGSGSGTEFTLTISSLQPDDFATYYCQHSNSLPLTF
GGGTKVEIK

B16-02  
VH (SEQ ID NO: 128)  
QVQLLESGGGLVQPGGSLRLSCAASGFTFSSYWMSWVRQAP
GKGLEWVANIKQDGSEK
YYVESVKGRFTISRDNAKNSLYLQMNSLRAEDTAVYYCARV
ALWDDAFDIWGQGTMVTVSS  
VL (SEQ ID NO: 32)  
DIQMTQSPSSLSASVGDRVTITCRASQSISSWLAWYQQKPG
KAPKLLIYKASSLESGV
PSRFSGSGSGTEFTLTISSLQPDDFATYYCQHSNSLPLTFG
GGTKVEIK

B16-03  
VH (SEQ ID NO: 127)  
QVQLLESGGGLVQPGGSLRLSCAASGFTFSSYWMSWVRQAP
GKGLEWVANIKQDASEK
YYVDSVKGRFTISRDNAKNSLYLQMNSLRAEDTAVYYCARV
ALWDDAFDIWGQGTMVTVSS  
VL (SEQ ID NO: 32)  
DIQMTQSPSSLSASVGDRVTITCRASQSISSWLAWYQQKPG
KAPKLLIYKASSLESGV
PSRFSGSGSGTEFTLTISSLQPDDFATYYCQHSNSLPLTFG
GGTKVEIK

B16-04  
VH (SEQ ID NO: 128)  
QVQLLESGGGLVQPGGSLRLSCAASGFTFSSYWMSWVRQAP
GKGLEWVANIKQDGSEK
YYVESVKGRFTISRDNAKNSLYLQMNSLRAEDTAVYYCARV
ALWDDAFDIWGQGTMVTVSS  
VL (SEQ ID NO: 129)  
DIQMTQSPSSLSASVGDRVTITCRASQSISSWLAWYQQKPG
KAPKLLIYKASSLESGV
PSRFSGSGSGTEFTLTISSLQPDDFATYYCQHSNALPLTFG
GGTKVEIK

B16-05  
VH (SEQ ID NO: 130)  
QVQLLESGGGLVQPGGSLRLSCAASGFTFSSYWMSWVRQAP
GKGLEWVANIKQDASEK
YYVESVKGRFTISRDNAKNSLYLQMNSLRAEDTAVYYCARV
ALWDDAFDIWGQGTMVTVSS  
VL (SEQ ID NO: 129)  
DIQMTQSPSSLSASVGDRVTITCRASQSISSWLAWYQQKPG
KAPKLLIYKASSLESGV
PSRFSGSGSGTEFTLTISSLQPDDFATYYCQHSNALPLTFG
GGTKVEIK

B16-06  
VH (SEQ ID NO: 128)  
QVQLLESGGGLVQPGGSLRLSCAASGFTFSSYWMSWVRQAP
GKGLEWVANIKQDGSEK
YYVESVKGRFTISRDNAKNSLYLQMNSLRAEDTAVYYCARV
ALWDDAFDIWGQGTMVTVSS  
VL (SEQ ID NO: 131)  
DIQMTQSPSSLSASVGDRVTITCRASQSISSWLAWYQQKPG
KAPKLLIYKASSLESGV
PSRFSGSGSGTEFTLTISSLQPDDFATYYCQHSQSLPLTFG
GGTKVEIK

B16-07  
VH (SEQ ID NO: 130)  
QVQLLESGGGLVQPGGSLRLSCAASGFTFSSYWMSWVRQAP
GKGLEWVANIKQDASEK
YYVESVKGRFTISRDNAKNSLYLQMNSLRAEDTAVYYCARV
ALWDDAFDIWGQGTMVTVSS  
VL (SEQ ID NO: 131)  
DIQMTQSPSSLSASVGDRVTITCRASQSISSWLAWYQQKPG
KAPKLLIYKASSLESGV
PSRFSGSGSGTEFTLTISSLQPDDFATYYCQHSQSLPLTFG
GGTKVEIK

Figure 4:
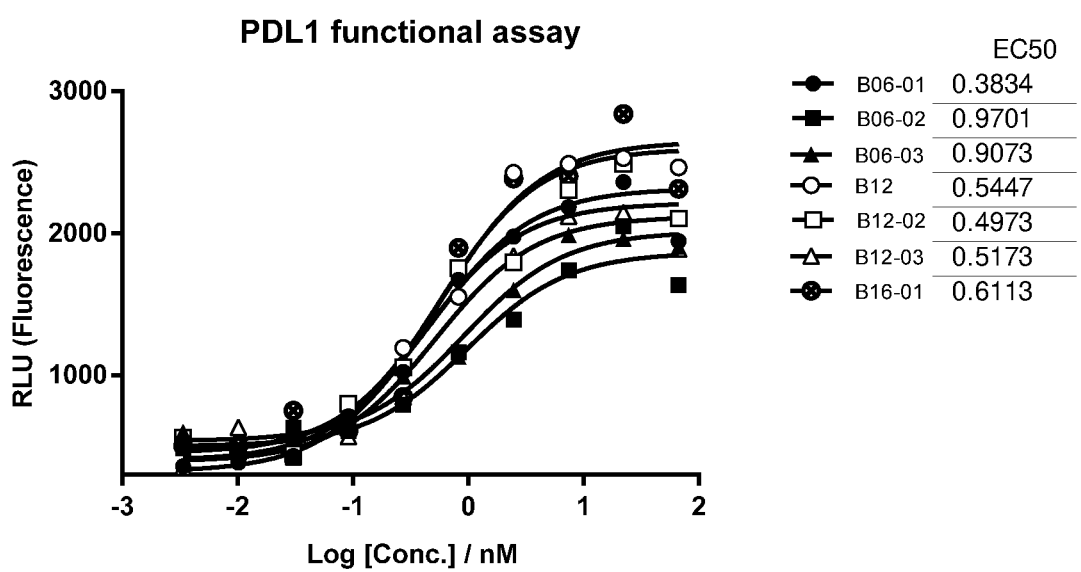
FIG. 4 shows the functional test results for the mutant antibodies.

To test the functional potency of the mutated anti-PDL1 antibodies to stimulate T cell response, hPD-1-expressed Jurkat cell assay were used as described above. As shown in FIG. 4, the representative mutants all had comparable functional potency, demonstrating the promise of these mutations in reducing the likelihood of post-translational modifications for the antibodies.

Example 5. Comparison to Reference Antibodies

One of the modified variants of B12, B12-01, was used as a representative to compare to known reference PD-L1 antibodies. The reference antibodies included atezolizumab (Tecentriq™), a fully humanized, Fc-engineered monoclonal antibody of IgG1 isotype, and avelumab (Bavencio™), a fully human monoclonal antibody.

Jurkat cells transfected with human PD-1 gene by lentivirus were used as the responder cells. The Raji-PD-L1 cells was used as the antigen presenting cells (APC). Staphylococcal Enterotoxins (SE) are used to stimulate TCR signal. In this system, ectopically expressed huPDL1 can suppress SE stimulated NF-AT-luciferase activity in Jurkat cells, while anti-PDL1 antibodies can reverse NF-AT-luciferase activity.

APCs were co-cultured with PD-1 expressing Jurkat T cells in the presence of SE stimulation. Anti-PDL1 antibodies were added at the beginning of the culture. 6 hr later, the resulting cells were evaluated for its luciferase activity.

The results are shown in FIG. 5. B12-01 exhibited significantly higher affinity than avelumab (EC50: 0.098 nM vs. 0.27 nM) in the cell-based assay and was also superior to Tecentriq (EC50: 0.098 nM vs. 0.12 nM).

Next, pilot developability characteristics including purity (size-exclusion chromatography (SEC)), isoelectric point (pI), melting temperature (Tm), and hydrophilicity (hydrophobic interaction chromatography (HIC)) were analyzed for B12-01 and compared with those of reference antibody Tecentriq. The results are shown in Table 3 below.

TABLE 3

Comparison of developability

| Sample ID # | B12-01 | Tecentriq |
|---|---|---|
| SEC (% monomer) | 93.79 | 99.61 |
| pI | 8.8 | 8.6 |
| Acid (%) | 35.6 | 38.7 |
| Main (%) | 58.7 | 47.7 |
| Basic (%) | 5.7 | 13.6 |
| Tm pH = 7.5 (° C.) | 68.5/78.0 | 59.5/81.5 |
| HIC (NH$_4$)$_2$SO$_4$(M) | 1.01 | 0.41 |

Interestingly, the results showed that B12-01 has higher hydrophilicity than Tecentriq. The difference in hydrophilicity can be attributed to their different amino acid compositions, and suggests that B12-01 has higher water solubility than Tecentriq. This property will give more flexibility during formulation development in the subsequent CMC stage.

Example 6. Binding Affinity by Biacore

In this example, the affinity of B12-01 to His-tagged human PD-L1 was assessed with Biacore T200.

Figure 6:
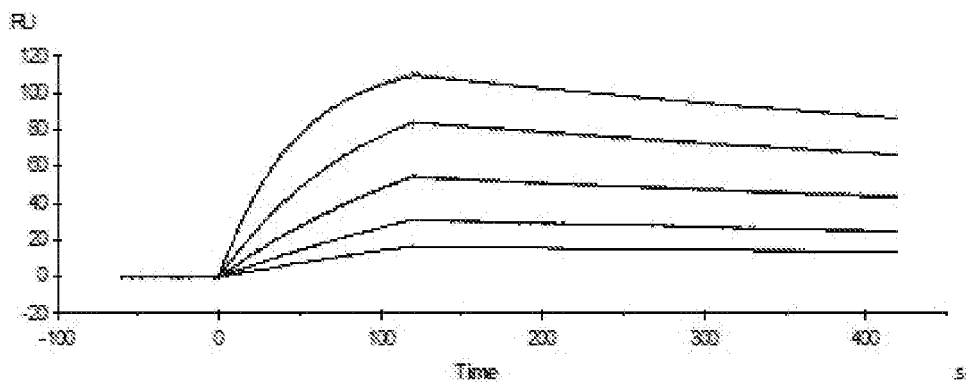
FIG. 6 shows that B12-01 has sub-nano molar affinity to PD-L1.

The analytes B12-01 were captured by protein A chip. Human PD-L1 protein (25 nM-1.56 nM) was injected over the captured analytes at a flow rate of 10 μL/min. The ligand was allowed to associate for 120 s and dissociate for 600 s. The data showed that B12-01 had sub-nano molar affinity to PD-L1 (9.48×10$^{-10}$ M, FIG. 6).

Example 7. Cross Species Reactivity

This example examined the binding activity of the antibodies to the PDL1 proteins from different species.

Figure 7:
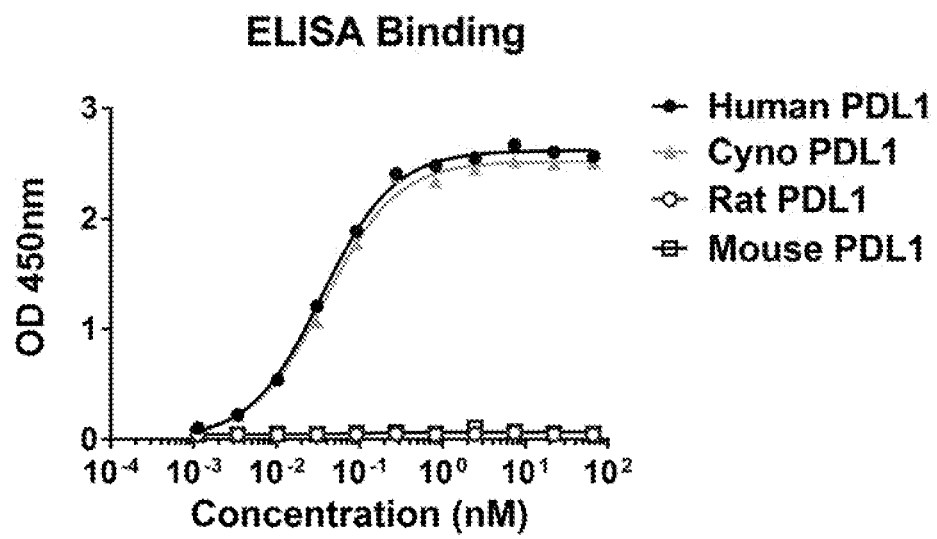
FIG. 7 shows that B12-01 has comparable binding capability to human PD-L1 and cyno PD-L1.

Human, cyno, rat and mouse PDL1-His proteins were coated at 0.5 μg/ml at 4° C. overnight. B12-01 was serially diluted at 1:3 ratio starting from 10 μg/ml and incubated with various PDL1 antigen for one hours at RT. The plates were washed and then incubated with HRP conjugated mouse anti-human IgG Fc antibody followed by development with TMB substrate and analyzed by spectrophotometer at OD 450 nm. As shown in FIG. 7, B12-01 showed comparable binding capability to human PD-L1 and cyno PD-L1. No specific binding of B12-01 to rat or mouse PDL1 was observed.

Example 8. Blocking of PD1-PDL1 Interaction

This example used Raji-PDL1 cells-based blocking assay to evaluate the ability of PDL1 antibodies to block the binding of PD1 protein to its cell ligand PDL1.

Figure 8:
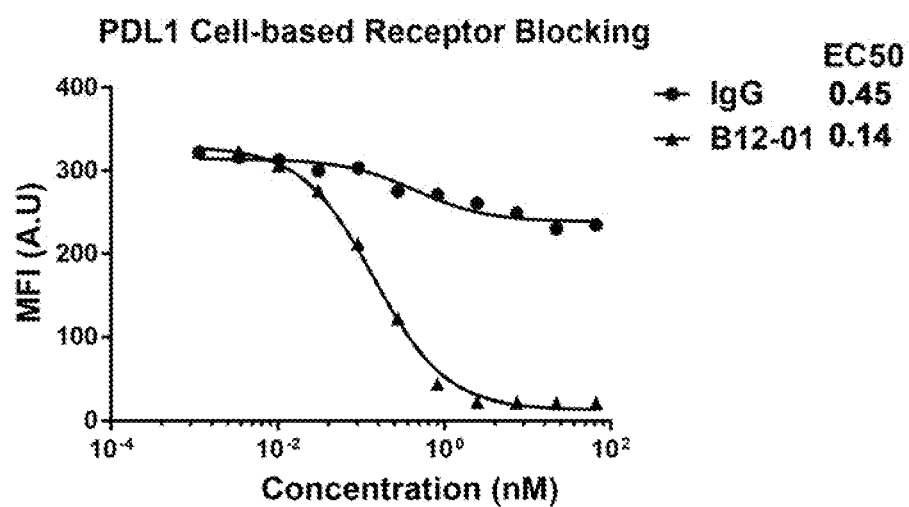
FIG. 8 shows that B12-01 effectively blocked the binding of PD1 protein to cell-surface PDL1.

Raji cells over-expressing human PDL1 were seeded into the 96 well plate at a concentration of 1×10$^5$ cells per well. The B12-01 antibody and the isotype control IgG were serially diluted from 10 μg/mL (1:3, 10 doses) with FACS buffer and incubated with the cells for 30 mins on ice. After washing, the diluted biotinylated Avi- and His-tag human PD1 protein (3 μg/mL) was incubated with the antibody-cell complex for 30 mins on ice and followed by Streptavidin-PE antibody detection. Fluorescence was measured by flow cytometry and analyzed by Flowjo software to determine the mean fluorescence intensities (WI). The data showed that the B12-01 antibody showed significant ability to block the binding of PD1 protein to cell-surface PDL1 (FIG. 8).

Example 9. In Vitro Function on T Cell Activation

This example assessed the in vitro function of the PDL1 antibodies on T cell activation, using a primary human mixture lymphocytes reaction (MLR) assay.

Figure 9:
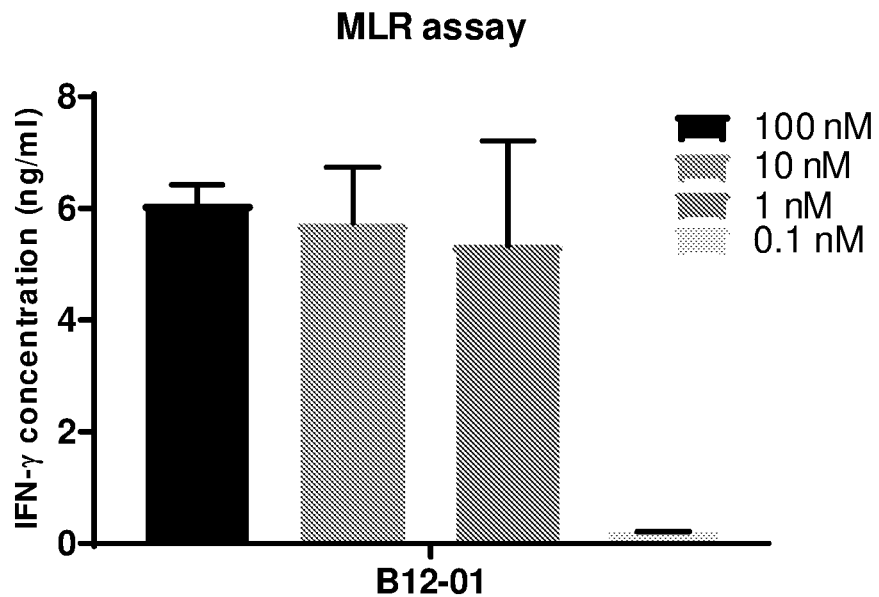
FIG. 9 shows that B12-01 significantly promoted human T cell activation in vitro.

Briefly, CD14$^+$ monocytes were isolated from human PBMCs of one donor and stimulated with GM-CSF and IL-4 for 7 days to differentiate into immature dendritic cells (imDCs). 2×10$^5$/ml CD4$^+$ T cells from human PBMC of another donor (1×10$^5$/well) was cocultured with imDCs (1×10$^4$/well) in the presence of serially diluted PDL1 antibody for 5 days. The concentration of IFN-γ in the supernatant was measured by ELISA. The result showed that B12-01 significantly promoted human T cell activation, as measured by IFNγ level in the culture medium (FIG. 9).

Example 10. In Vivo Efficacy of PDL1 Antibody

This example employed human PDL1 extracellular domain (ECD) transgenic mice to evaluate the in vivo efficacy of PDL1 antibody.

Figure 10:
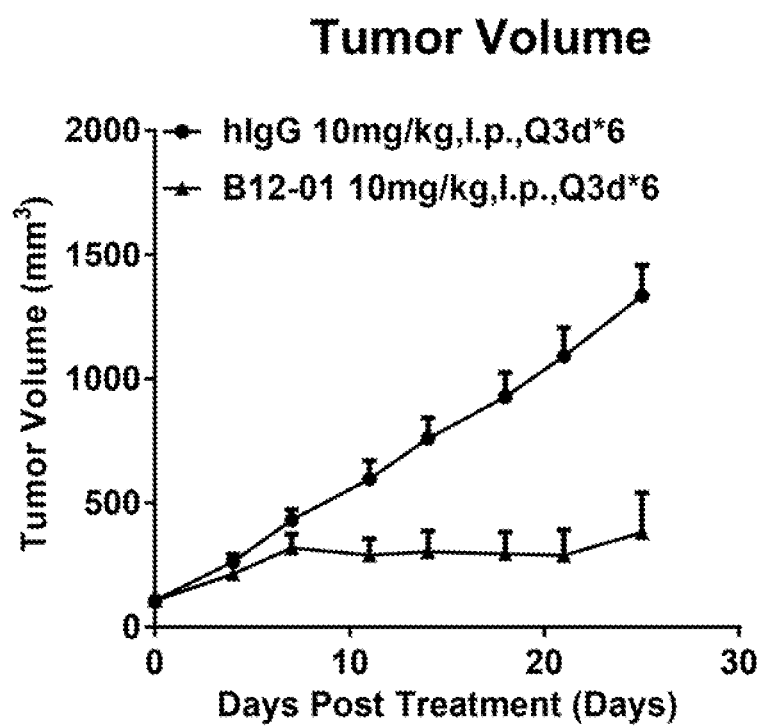
FIG. 10 shows the in vivo efficacy of B12-01 in inhibiting tumor growth.

Mouse colon adenocarcinoma cells MC38 engineered to express human PDL1(MC38-hPD-L1) were subcutaneously engrafted into hPDL1 humanized mice. Mice were divided into two groups when the average tumor volume reached about 100 mm$^3$ and intraperitoneally administered with B12-01 antibody or isotype IgG control at 10 mg/kg every 3 days for 6 times. Tumor volumes were monitored by caliper measurement twice a week during the experiment. The result showed that B12-01 effectively inhibited tumor growth compared with those of IgG group (FIG. 10).

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference

What is claimed is:

1. An antibody or antigen-binding fragment thereof, wherein the antibody or fragment thereof has specificity to a human Programmed death-ligand 1 (PD-L1) protein and comprises a heavy chain variable region (VH) comprising a VH CDR1, a VH CDR2, and a VH CDR3, and a light chain variable region (VL) comprising a VL CDR1, a VL CDR2, and a VL CDR3, wherein:
the VH CDR1 comprises the amino acid sequence of SEQ ID NO:37,
the VH CDR2 comprises the amino acid sequence of SEQ ID NO:46, 135, 136, 137, 143 or 144,
the VH CDR3 comprises the amino acid sequence of SEQ ID NO:63,
the VL CDR1 comprises the amino acid sequence of SEQ ID NO:76,
the VL CDR2 comprises the amino acid sequence of SEQ ID NO:83, and
the VL CDR3 comprises the amino acid sequence of SEQ ID NO:97.

2. The antibody or fragment thereof of claim 1, wherein:
the VH CDR1 comprises the amino acid sequence of SEQ ID NO:37,
the VH CDR2 comprises the amino acid sequence of SEQ ID NO:46,
the VH CDR3 comprises the amino acid sequence of SEQ ID NO:63,
the VL CDR1 comprises the amino acid sequence of SEQ ID NO:76,
the VL CDR2 comprises the amino acid sequence of SEQ ID NO:83, and
the VL CDR3 comprises the amino acid sequence of SEQ ID NO:97.

3. The antibody or fragment thereof of claim 1, wherein the VH comprises the amino acid sequence of SEQ ID NO:23, 124, 126, 127, 128, 130, 140, or 145, and the VL comprises the amino acid sequence of SEQ ID NO:24 or 125.

4. The antibody or fragment thereof of claim 1, wherein the VH comprises the amino acid sequence of SEQ ID NO:124 or a first amino acid sequence having at least 95% sequence identity to SEQ ID NO:124, and the VL comprises the amino acid sequence of SEQ ID NO: 125 or a second amino acid sequence having at least 95% sequence identity to SEQ ID NO:125.

5. An antibody or antigen-binding fragment thereof, wherein the antibody or fragment thereof has specificity to a human Programmed death-ligand 1 (PD-L1) protein and comprises a heavy chain variable region (VH) comprising a VH CDR1, a VH CDR2, and a VH CDR3, and a light chain variable region (VL) comprising a VL CDR1, a VL CDR2, and a VL CDR3, wherein:
the VH CDR1 comprises the amino acid sequence of SEQ ID NO:38 or 132,
the VH CDR2 comprises the amino acid sequence of SEQ ID NO:47, 133 or 134,
the VH CDR3 comprises the amino acid sequence of SEQ ID NO:57,
the VL CDR1 comprises the amino acid sequence of SEQ ID NO:72,
the VL CDR2 comprises the amino acid sequence of SEQ ID NO:84, and
the VL CDR3 comprises the amino acid sequence of SEQ ID NO:93.

6. The antibody or fragment thereof of claim 5, wherein the VH comprises the amino acid sequence of SEQ ID NO: 11, 121, 122 or 123 or a first amino acid sequence having at least 95% sequence identity to SEQ ID NO: 11, 121, 122 or 123, and the VL comprises the amino acid sequence of SEQ ID NO:12 or a second amino acid sequence having at least 95% sequence identity to SEQ ID NO:12.

7. An antibody or antigen-binding fragment thereof, wherein the antibody or fragment thereof has specificity to a human Programmed death-ligand 1 (PD-L1) protein and comprises a heavy chain variable region (VH) comprising a VH CDR1, a VH CDR2, and a VH CDR3, and a light chain variable region (VL) comprising a VL CDR1, a VL CDR2, and a VL CDR3, wherein:
the VH CDR1 comprises the amino acid sequence of SEQ ID NO:37,
the VH CDR2 comprises the amino acid sequence of SEQ ID NO:46, 135, 136, 137, 143 or 144,
the VH CDR3 comprises the amino acid sequence of SEQ ID NO:63,
the VL CDR1 comprises the amino acid sequence of SEQ ID NO:71,
the VL CDR2 comprises the amino acid sequence of SEQ ID NO:83, and
the VL CDR3 comprises the amino acid sequence of SEQ ID NO:101, 138, or 139.

8. The antibody or fragment thereof of claim 7, wherein the VH comprises the amino acid sequence of SEQ ID NO:31, 124, 126, 127, 128, 130, 140, or 145 or a first amino acid sequence having at least 95% sequence identity to SEQ ID NO: 31, 124, 126, 127, 128, 130, 140, or 145, and the VL comprises the amino acid sequence of SEQ ID NO:32, 129 or 131 or a second amino acid sequence having at least 95% sequence identity to SEQ ID NO:32, 129 or 131.

9. The antibody or fragment thereof of claim 1, further comprising a heavy chain constant region, a light chain constant region, an Fc region, or the combination thereof.

10. The antibody or fragment thereof of claim 1, wherein the antibody or fragment thereof is a fully human antibody.

11. A bispecific antibody comprising a first antigen binding fragment of claim 1 and a second antigen binding fragment having specificity to an antigen that is not PD-L1.

12. A composition comprising the antibody or fragment thereof of claim 1 and a pharmaceutically acceptable carrier.

13. One or more polynucleotide encoding the antibody or fragment thereof of claim 1.

14. An isolated cell comprising one or more polynucleotide encoding the antibody or fragment thereof of claim 1.

15. A method of treating cancer or infection in a patient in need thereof, comprising administering to the patient an effective amount of the antibody or fragment thereof of claim 1.

16. The method of claim 15, wherein the cancer is a solid tumor.

17. The method or use of claim 16, wherein the cancer is selected from the group consisting of bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer and thyroid cancer.

18. The method of claim 15, wherein the infection is viral infection, bacterial infection, fungal infection or infection by a parasite.

\* \* \* \* \*

SEQUENCE LISTING

<160> NUMBER OF SEQ ID NOS: 145

<210> SEQ ID NO 1
<211> LENGTH: 116
<212> TYPE: PRT
<213> ORGANISM: Artificial Sequence
<220> FEATURE:
<223> OTHER INFORMATION: Synthetic

<400> SEQUENCE: 1

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Ser His
            20                  25                  30

Trp Leu Ala Trp Val Arg Gln Ala Pro Gly Lys Gly Leu Glu Trp Val
        35                  40                  45

Ala Ser Ile His Gln Asp Ala Ser Leu Glu Phe Tyr Val Asp Ser Val
    50                  55                  60

Glu Gly Arg Phe Thr Ile Ser Arg Asp Asn Ser Lys Arg Ser Leu Phe
65                  70                  75                  80

Leu Gln Met Asn Asn Leu Arg Val Glu Asp Thr Ala Val Tyr Tyr Cys
                85                  90                  95

Ala Arg Gly Asp Asn Gln Phe Asp Asn Trp Gly Gln Gly Thr Leu Val
            100                 105                 110

Thr Val Ser Ala
        115
```

<210> SEQ ID NO 2
<211> LENGTH: 107
<212> TYPE: PRT
<213> ORGANISM: Artificial Sequence
<220> FEATURE:
<223> OTHER INFORMATION: Synthetic

<400> SEQUENCE: 2

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Pro Gly Thr Lys Val Asp Ile Lys
            100                 105
```

<210> SEQ ID NO 3
<211> LENGTH: 125
<212> TYPE: PRT
<213> ORGANISM: Artificial Sequence
<220> FEATURE:
<223> OTHER INFORMATION: Synthetic

<400> SEQUENCE: 3

```
Gln Val Gln Leu Leu Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Thr Tyr
            20                  25                  30

Ile Ile Asn Trp Val Arg Gln Ala Pro Gly Lys Gly Leu Glu Trp Val
        35                  40                  45

Ser Ser Val Ala Ala Ser Gly Asp Tyr Ala Tyr Ala Asn Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Ser Gly Tyr Tyr Leu Ser Pro Asn Asp Ala Phe
            100                 105                 110

Asp Ile Trp Gly Gln Gly Thr Met Val Thr Val Ser Ala
            115                 120                 125

<210> SEQ ID NO 4
<211> LENGTH: 107
<212> TYPE: PRT
<213> ORGANISM: Artificial Sequence
<220> FEATURE:
<223> OTHER INFORMATION: Synthetic

<400> SEQUENCE: 4

Asn Ile Gln Leu Thr Gln Ser Pro Ser Ser Leu Ser Ala Ser Leu Gly
1               5                   10                  15

Asp Arg Val Thr Ile Thr Cys Arg Ala Ser Gln Thr Ile Ser Arg Tyr
            20                  25                  30

Leu Asn Trp Tyr Gln Gln Lys Pro Gly Lys Ala Pro Glu Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Thr Phe Gly Gly Gly Thr Lys Val Glu Ile Lys
            100                 105

<210> SEQ ID NO 5
<211> LENGTH: 119
<212> TYPE: PRT
<213> ORGANISM: Artificial Sequence
<220> FEATURE:
<223> OTHER INFORMATION: Synthetic

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

```
                85                  90                  95
Ala Arg Val Val Arg Phe Asn Asp Ala Phe Asp Ile Trp Gly Gln Gly
            100                 105                 110

Thr Met Val Thr Val Ser Ala
        115

<210> SEQ ID NO 6
<211> LENGTH: 107
<212> TYPE: PRT
<213> ORGANISM: Artificial Sequence
<220> FEATURE:
<223> OTHER INFORMATION: Synthetic

<400> SEQUENCE: 6

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Asp Thr Trp
            20                  25                  30

Leu Ala Trp Tyr Gln Gln Lys Pro Gly Lys Ala Pro Lys Leu Leu Ile
        35                  40                  45

His Asn Ala Ser Thr Leu Lys Ser Gly Val Ser Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 7
<211> LENGTH: 119
<212> TYPE: PRT
<213> ORGANISM: Artificial Sequence
<220> FEATURE:
<223> OTHER INFORMATION: Synthetic

<400> SEQUENCE: 7

Gln Val Gln Leu Leu Asp Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Thr Met Leu Trp Asp Asp Ala Phe Asp Ile Trp Gly Gln Gly
            100                 105                 110

Thr Met Val Thr Val Ser Ala
        115

<210> SEQ ID NO 8
<211> LENGTH: 107
<212> TYPE: PRT
<213> ORGANISM: Artificial Sequence
<220> FEATURE:
```

<223> OTHER INFORMATION: Synthetic

<400> SEQUENCE: 8

Asp Ile Gln Leu Thr Gln Ser Pro Ser Thr Leu Ser Ala Ser Val Gly
1               5                   10                  15

Asp Arg Val Thr Ile Thr Cys Arg Ala Ser Glu Ser Ile Ser Ser Trp
            20                  25                  30

Leu Ala Trp Tyr Gln Gln Lys Pro Gly Lys Val Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 9
<211> LENGTH: 121
<212> TYPE: PRT
<213> ORGANISM: Artificial Sequence
<220> FEATURE:
<223> OTHER INFORMATION: Synthetic

<400> SEQUENCE: 9

Glu Val Gln Leu Val Glu Thr Gly Arg Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Tyr Gly Asp Asp Ala Phe Asp Ile Trp Gly
            100                 105                 110

Gln Gly Thr Met Val Thr Val Ser Ala
        115                 120

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Asn Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly

```
                    50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Thr Tyr Ser Leu Pro Leu
                     85                  90                  95

Thr Phe Gly Gln Gly Thr Arg Val Gly Ile Lys
                100                 105
```

<210> SEQ ID NO 11
<211> LENGTH: 118
<212> TYPE: PRT
<213> ORGANISM: Artificial Sequence
<220> FEATURE:
<223> OTHER INFORMATION: Synthetic

<400> SEQUENCE: 11

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Ser
                 20                  25                  30

Trp Ile His Trp Val Arg Gln Ala Pro Gly Lys Gly Leu Glu Trp Val
             35                  40                  45

Ala Trp Ile Ser Pro Tyr Gly Gly Ser Thr Tyr Tyr Ala Asp Ser Val
         50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
                100                 105                 110

Leu Val Thr Val Ser Ala
            115
```

<210> SEQ ID NO 12
<211> LENGTH: 107
<212> TYPE: PRT
<213> ORGANISM: Artificial Sequence
<220> FEATURE:
<223> OTHER INFORMATION: Synthetic

<400> SEQUENCE: 12

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Tyr
                 20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Asp Arg Phe Ser Gly
         50                  55                  60

Ser Gly Ser Gly Thr Asp Phe Thr Leu Thr Ile Ser Ser Leu Gln Ala
 65                  70                  75                  80

Glu Asp Val Ala Val Tyr Tyr Cys Gln Gln Tyr Leu Ser Val Pro Tyr
                 85                  90                  95

Thr Phe Gly Gln Gly Thr Lys Val Glu Ile Lys
                100                 105
```

<210> SEQ ID NO 13
<211> LENGTH: 119

```
<212> TYPE: PRT
<213> ORGANISM: Artificial Sequence
<220> FEATURE:
<223> OTHER INFORMATION: Synthetic

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Cys Gly Tyr Asp Asp Ala Phe Asp Ile Trp Gly Gln Gly
            100                 105                 110

Thr Met Val Thr Val Ser Ala
        115

<210> SEQ ID NO 14
<211> LENGTH: 107
<212> TYPE: PRT
<213> ORGANISM: Artificial Sequence
<220> FEATURE:
<223> OTHER INFORMATION: Synthetic

<400> SEQUENCE: 14

Asn Ile Gln Met Thr His Ser Pro Ser Thr Leu Ser Ala Ser Val Gly
1               5                   10                  15

Asp Arg Val Thr Ile Ser Cys Arg Ala Ser Gln Ser Ile Ser Thr Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Leu
                85                  90                  95

Thr Phe Gly Gly Gly Thr Lys Val Glu Ile Lys
            100                 105

<210> SEQ ID NO 15
<211> LENGTH: 122
<212> TYPE: PRT
<213> ORGANISM: Artificial Sequence
<220> FEATURE:
<223> OTHER INFORMATION: Synthetic

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Val Gly Ser Gly Phe Thr Phe Ser Asp His
            20                  25                  30

Tyr Met Asp Trp Val Arg Gln Ala Pro Gly Lys Gly Leu Glu Trp Val
```

35                  40                  45
Ser Ser Ile Ser Ser Ser Ser Tyr Ile Tyr Tyr Ala Asp Ser Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly Arg Val Gly Ala Thr Asn Arg Phe Gly Met Asp Val Trp
            100                 105                 110
Gly Gln Gly Thr Met Val Thr Val Ser Ala
            115                 120

<210> SEQ ID NO 16
<211> LENGTH: 106
<212> TYPE: PRT
<213> ORGANISM: Artificial Sequence
<220> FEATURE:
<223> OTHER INFORMATION: Synthetic

<400> SEQUENCE: 16

Asp Ile Gln Met Ile Gln Ser Pro Ser Ser Val Ser Ala Ser Val Gly
1               5                   10                  15
Asp Arg Val Thr Ile Thr Cys Arg Ala Ser Glu Ser Ile Ser Arg Trp
            20                  25                  30
Leu Ala Trp Tyr Gln Gln Lys Pro Gly Lys Ala Pro Lys Leu Leu Ile
        35                  40                  45
Tyr Ala Ala Ser Asn Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Ala Glu Ser Phe Pro Ser
                85                  90                  95
Phe Gly Gln Gly Thr Arg Leu Glu Ile Lys
            100                 105

<210> SEQ ID NO 17
<211> LENGTH: 119
<212> TYPE: PRT
<213> ORGANISM: Artificial Sequence
<220> FEATURE:
<223> OTHER INFORMATION: Synthetic

<400> SEQUENCE: 17

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Trp Met Ser Trp Val Arg Gln Ala Pro Gly Lys Gly Leu Glu Trp Val
        35                  40                  45
Ala Asn Ile Lys Gln Asp Gly Ser Glu Lys Tyr Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Glu Asp Phe Trp Ser Gly Tyr Gln Asp Val Trp Gly Gln Gly
            100                 105                 110

```
Thr Met Val Thr Val Ser Ala
        115

<210> SEQ ID NO 18
<211> LENGTH: 107
<212> TYPE: PRT
<213> ORGANISM: Artificial Sequence
<220> FEATURE:
<223> OTHER INFORMATION: Synthetic

<400> SEQUENCE: 18

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 19
<211> LENGTH: 122
<212> TYPE: PRT
<213> ORGANISM: Artificial Sequence
<220> FEATURE:
<223> OTHER INFORMATION: Synthetic

<400> SEQUENCE: 19

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Gly Ala Glu Asp Thr Ala Met Tyr Tyr Cys
                85                  90                  95

Ala Arg Ala Thr Val Lys Tyr Gly Gly Asp Asp Ala Phe Asp Ile Trp
            100                 105                 110

Gly Gln Gly Thr Met Val Thr Val Ser Ala
        115                 120

<210> SEQ ID NO 20
<211> LENGTH: 107
<212> TYPE: PRT
<213> ORGANISM: Artificial Sequence
<220> FEATURE:
<223> OTHER INFORMATION: Synthetic

<400> SEQUENCE: 20

Asn Ile Gln Leu Thr Gln Ser Pro Ser Thr Leu Ser Ala Ser Val Gly
```

```
            1               5                  10                 15
        Asp Arg Val Thr Ile Thr Cys Arg Ala Ser Gln Ser Ile Ser Asp Trp
                        20                  25                 30

Leu Ala Trp Tyr Gln Gln Lys Pro Gly Lys Ala Pro Asn Leu Leu Ile
                        35                  40                 45

Tyr Lys Ala Ser Ser Leu Glu Ser Gly Val Pro Ser Arg Phe Ser Gly
                        50                  55                 60

Ser Gly Ser Gly Thr Asp Phe Thr Leu Thr Ile Ser Ser Leu Gln Pro
        65                      70                  75                 80

Glu Asp Phe Ala Thr Tyr Tyr Cys Gln Gln Ser Phe Ser Thr Pro Phe
                        85                  90                 95

Thr Phe Gly Pro Gly Thr Lys Val Asp Ile Lys
                        100                 105
```

<210> SEQ ID NO 21
<211> LENGTH: 122
<212> TYPE: PRT
<213> ORGANISM: Artificial Sequence
<220> FEATURE:
<223> OTHER INFORMATION: Synthetic

<400> SEQUENCE: 21

```
        Glu Val Gln Leu Leu Glu Ser Gly Ala Glu Val Lys Lys Pro Gly Ser
        1               5                  10                 15

Ser Val Lys Val Ser Cys Lys Ala Ser Gly Gly Thr Phe Ser Ser Tyr
                        20                  25                 30

Ala Ile Ser Trp Val Arg Gln Ala Pro Gly Gln Gly Leu Glu Trp Met
                        35                  40                 45

Gly Gly Ile Ile Pro Ile Phe Gly Thr Ala Asn Tyr Ala Gln Lys Phe
                        50                  55                 60

Gln Gly Arg Val Thr Ile Thr Ala Asp Glu Ser Thr Ser Thr Ala Tyr
        65                      70                  75                 80

Met Glu Leu Ser Ser Leu Arg Ser Glu Asp Thr Ala Val Tyr Tyr Cys
                        85                  90                 95

Ala Arg Arg Thr Asp Ser Tyr Gly Tyr Ser Asp Ala Phe Asp Ile Trp
                        100                 105                110

Gly Gln Gly Thr Met Val Thr Val Ser Ala
                        115                 120
```

<210> SEQ ID NO 22
<211> LENGTH: 107
<212> TYPE: PRT
<213> ORGANISM: Artificial Sequence
<220> FEATURE:
<223> OTHER INFORMATION: Synthetic

<400> SEQUENCE: 22

```
        Asp Ile Gln Leu Thr Gln Ser Pro Ser Ser Leu Ser Ala Ser Val Gly
        1               5                  10                 15

Asp Arg Val Thr Ile Thr Cys Arg Ala Ser Gln Ser Ile Ser Ser Tyr
                        20                  25                 30

Leu Asn Trp Tyr Gln Gln Lys Pro Gly Lys Ala Pro Lys Leu Leu Ile
                        35                  40                 45

Tyr Ala Ala Ser Ser Leu Gln Ser Gly Val Pro Ser Arg Phe Ser Gly
                        50                  55                 60

Ser Gly Ser Gly Thr Asp Phe Thr Leu Thr Ile Ser Ser Leu Gln Pro
        65                      70                  75                 80
```

```
Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 23
<211> LENGTH: 119
<212> TYPE: PRT
<213> ORGANISM: Artificial Sequence
<220> FEATURE:
<223> OTHER INFORMATION: Synthetic

<400> SEQUENCE: 23

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Ala Leu Trp Asp Asp Ala Phe Asp Ile Trp Gly Gln Gly
            100                 105                 110

Thr Met Val Thr Val Ser Ala
        115

<210> SEQ ID NO 24
<211> LENGTH: 107
<212> TYPE: PRT
<213> ORGANISM: Artificial Sequence
<220> FEATURE:
<223> OTHER INFORMATION: Synthetic

<400> SEQUENCE: 24

Asn Ile Gln Leu Thr Gln Ser Pro Ser Thr Leu Ser Ala Ser Val Gly
1               5                   10                  15

Asp Arg Val Ile Ile Thr Cys Arg Ala Ser Arg Gly Ile Ser Ser Trp
            20                  25                  30

Leu Ala Trp Tyr Gln Gln Lys Pro Gly Lys Ala Pro Asn Leu Leu Ile
        35                  40                  45

Ser Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Ile Pro Leu
                85                  90                  95

Thr Phe Gly Gly Gly Thr Lys Val Glu Ile Lys
            100                 105

<210> SEQ ID NO 25
<211> LENGTH: 122
<212> TYPE: PRT
<213> ORGANISM: Artificial Sequence
<220> FEATURE:
<223> OTHER INFORMATION: Synthetic
```

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Ser Thr Val Lys Tyr Gly Ala Asp Asp Ala Phe Asp Ile Trp
            100                 105                 110

Gly Gln Gly Ala Met Val Thr Val Ser Ala
        115                 120

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

Asn Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 27
<211> LENGTH: 119
<212> TYPE: PRT
<213> ORGANISM: Artificial Sequence
<220> FEATURE:
<223> OTHER INFORMATION: Synthetic

<400> SEQUENCE: 27

Glu Val Gln Leu Leu Glu Ser Gly Gly Gly Val Gln Pro Gly Arg
1               5                   10                  15

Ser Leu Arg Leu Ser Cys Ala Ala Ser Gly Phe Ser Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Val Arg Phe Asn Asp Ala Phe Asp Ile Trp Gly Gln Gly
            100                 105                 110

Thr Met Val Thr Val Ser Ala
        115

<210> SEQ ID NO 28
<211> LENGTH: 107
<212> TYPE: PRT
<213> ORGANISM: Artificial Sequence
<220> FEATURE:
<223> OTHER INFORMATION: Synthetic

<400> SEQUENCE: 28

Asn Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 29
<211> LENGTH: 120
<212> TYPE: PRT
<213> ORGANISM: Artificial Sequence
<220> FEATURE:
<223> OTHER INFORMATION: Synthetic

<400> SEQUENCE: 29

Glu Val Gln Leu Leu Glu Ser Gly Gly Gly Leu Val Lys Pro Gly Gly
1               5                   10                  15

Ser Leu Arg Leu Ser Cys Ser Ala Ser Gly Phe Thr Phe Ser Val Tyr
            20                  25                  30

Tyr Met Ala Trp Ile Arg Gln Ala Pro Gly Glu Gly Leu Glu Trp Ile
        35                  40                  45

Ser Tyr Thr Ser Asn Gly Asp Gly Asp Ile Thr Tyr Tyr Ala Asp Ser
    50                  55                  60

Val Lys Asp Arg Phe Thr Ile Ser Arg Asp Asn Ala Lys Asn Ser Leu
65                  70                  75                  80

Leu Leu Gln Met Asn Ser Leu Arg Asp Glu Asp Thr Ala Val Tyr Tyr
                85                  90                  95

Cys Val Arg Ala Ala Arg Ser Gly Tyr Tyr Asn Asp Tyr Trp Gly Gln
            100                 105                 110

Gly Thr Leu Val Thr Val Ser Ala
        115                 120

<210> SEQ ID NO 30

<211> LENGTH: 108
<212> TYPE: PRT
<213> ORGANISM: Artificial Sequence
<220> FEATURE:
<223> OTHER INFORMATION: Synthetic

<400> SEQUENCE: 30

```
Asp Ile Gln Leu Thr Gln Ser Pro Ser Ser Leu Ser Ala Ser Val Gly
1               5                   10                  15

Asp Arg Val Thr Met Thr Cys Arg Ala Ser Gln Phe Ile Ser Lys Tyr
            20                  25                  30

Val Asn Trp Tyr Gln Gln Lys Pro Gly Lys Ala Pro Lys Val Leu Ile
        35                  40                  45

Tyr Gly Ala Ser Ile Leu Glu Thr Gly Val Pro Ser Arg Phe Ser Gly
50                  55                  60

Ser Gly Phe Gly Thr Asp Phe Thr Phe Thr Ile Ser Ser Leu Gln Pro
65                  70                  75                  80

Glu Asp Phe Ala Thr Tyr Tyr Cys Gln Gln Thr His Ser Thr Pro Arg
                85                  90                  95

Gly Val Phe Gly Gln Gly Thr Arg Val Glu Val Lys
            100                 105
```

<210> SEQ ID NO 31
<211> LENGTH: 119
<212> TYPE: PRT
<213> ORGANISM: Artificial Sequence
<220> FEATURE:
<223> OTHER INFORMATION: Synthetic

<400> SEQUENCE: 31

```
Gln Val Gln Leu Leu Asp Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Ala Leu Trp Asp Asp Ala Phe Asp Ile Trp Gly Gln Gly
            100                 105                 110

Thr Met Val Thr Val Ser Ala
        115
```

<210> SEQ ID NO 32
<211> LENGTH: 107
<212> TYPE: PRT
<213> ORGANISM: Artificial Sequence
<220> FEATURE:
<223> OTHER INFORMATION: Synthetic

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30
```

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln His Ser Asn Ser Leu Pro Leu
                 85                  90                  95

Thr Phe Gly Gly Gly Thr Lys Val Glu Ile Lys
            100                 105

<210> SEQ ID NO 33
<211> LENGTH: 121
<212> TYPE: PRT
<213> ORGANISM: Artificial Sequence
<220> FEATURE:
<223> OTHER INFORMATION: Synthetic

<400> SEQUENCE: 33

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Asn
             20                  25                  30

Ala Met Ser Trp Val Arg Gln Ala Pro Gly Lys Gly Leu Glu Trp Val
         35                  40                  45

Ser Ala Val Gly Gly Gly Val Asn Thr Tyr Tyr Ala Asp Ser Val
     50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Lys Gly Tyr Ser Asn Ser Cys Ile Asp Tyr Trp Gly
            100                 105                 110

Gln Gly Thr Leu Val Thr Val Ser Ala
            115                 120

<210> SEQ ID NO 34
<211> LENGTH: 108
<212> TYPE: PRT
<213> ORGANISM: Artificial Sequence
<220> FEATURE:
<223> OTHER INFORMATION: Synthetic

<400> SEQUENCE: 34

Asn Ile Gln Leu Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Pro
                 85                  90                  95

Phe Thr Phe Gly Pro Gly Thr Lys Val Asp Ile Lys
            100                 105

```
<210> SEQ ID NO 35
<211> LENGTH: 5
<212> TYPE: PRT
<213> ORGANISM: Artificial Sequence
<220> FEATURE:
<223> OTHER INFORMATION: Synthetic

<400> SEQUENCE: 35

Ser His Trp Leu Ala
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic

<400> SEQUENCE: 36

Thr Tyr Ile Ile Asn
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic

<400> SEQUENCE: 37

Ser Tyr Trp Met Ser
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic

<400> SEQUENCE: 38

Asp Ser Trp Ile His
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic

<400> SEQUENCE: 39

Asp His Tyr Met Asp
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic

<400> SEQUENCE: 40

Ser Tyr Ala Ile Ser
1               5
```

<210> SEQ ID NO 41
<211> LENGTH: 5
<212> TYPE: PRT
<213> ORGANISM: Artificial Sequence
<220> FEATURE:
<223> OTHER INFORMATION: Synthetic

<400> SEQUENCE: 41

Val Tyr Tyr Met Ala
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic

<400> SEQUENCE: 42

Ser Asn Ala Met Ser
1               5

<210> SEQ ID NO 43
<211> LENGTH: 17
<212> TYPE: PRT
<213> ORGANISM: Artificial Sequence
<220> FEATURE:
<223> OTHER INFORMATION: Synthetic

<400> SEQUENCE: 43

Ser Ile His Gln Asp Ala Ser Leu Glu Phe Tyr Val Asp Ser Val Glu
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: Synthetic

<400> SEQUENCE: 44

Ser Val Ala Ala Ser Gly Asp Tyr Ala Tyr Tyr Ala Asn Ser Val Lys
1               5                   10                  15

Gly

<210> SEQ ID NO 45
<211> LENGTH: 17
<212> TYPE: PRT
<213> ORGANISM: Artificial Sequence
<220> FEATURE:
<223> OTHER INFORMATION: Synthetic

<400> SEQUENCE: 45

Asn Ile Lys Glu Asp Gly Ser Glu Lys Tyr Tyr Val Asp Ser Val Lys
1               5                   10                  15

Gly

<210> SEQ ID NO 46
<211> LENGTH: 17
<212> TYPE: PRT
<213> ORGANISM: Artificial Sequence
<220> FEATURE:
<223> OTHER INFORMATION: Synthetic

```
<400> SEQUENCE: 46

Asn Ile Lys Gln Asp Gly Ser Glu Lys Tyr Tyr Val Asp Ser Val Lys
1               5                   10                  15

Gly

<210> SEQ ID NO 47
<211> LENGTH: 17
<212> TYPE: PRT
<213> ORGANISM: Artificial Sequence
<220> FEATURE:
<223> OTHER INFORMATION: Synthetic

<400> SEQUENCE: 47

Trp Ile Ser Pro Tyr Gly Gly Ser Thr Tyr Tyr Ala Asp Ser Val Lys
1               5                   10                  15

Gly

<210> SEQ ID NO 48
<211> LENGTH: 17
<212> TYPE: PRT
<213> ORGANISM: Artificial Sequence
<220> FEATURE:
<223> OTHER INFORMATION: Synthetic

<400> SEQUENCE: 48

Ser Ile Ser Ser Ser Ser Ser Tyr Ile Tyr Tyr Ala Asp Ser Val Lys
1               5                   10                  15

Gly

<210> SEQ ID NO 49
<211> LENGTH: 17
<212> TYPE: PRT
<213> ORGANISM: Artificial Sequence
<220> FEATURE:
<223> OTHER INFORMATION: Synthetic

<400> SEQUENCE: 49

Gly Ile Ile Pro Ile Phe Gly Thr Ala Asn Tyr Ala Gln Lys Phe Gln
1               5                   10                  15

Gly

<210> SEQ ID NO 50
<211> LENGTH: 18
<212> TYPE: PRT
<213> ORGANISM: Artificial Sequence
<220> FEATURE:
<223> OTHER INFORMATION: Synthetic

<400> SEQUENCE: 50

Tyr Thr Ser Asn Gly Asp Gly Asp Ile Thr Tyr Tyr Ala Asp Ser Val
1               5                   10                  15

Lys Asp

<210> SEQ ID NO 51
<211> LENGTH: 17
<212> TYPE: PRT
<213> ORGANISM: Artificial Sequence
<220> FEATURE:
<223> OTHER INFORMATION: Synthetic

<400> SEQUENCE: 51

Ala Val Gly Gly Gly Gly Val Asn Thr Tyr Tyr Ala Asp Ser Val Lys
1               5                   10                  15
```

Gly

<210> SEQ ID NO 52
<211> LENGTH: 7
<212> TYPE: PRT
<213> ORGANISM: Artificial Sequence
<220> FEATURE:
<223> OTHER INFORMATION: Synthetic

<400> SEQUENCE: 52

Gly Asp Asn Gln Phe Asp Asn
1               5

<210> SEQ ID NO 53
<211> LENGTH: 16
<212> TYPE: PRT
<213> ORGANISM: Artificial Sequence
<220> FEATURE:
<223> OTHER INFORMATION: Synthetic

<400> SEQUENCE: 53

Asp Arg Ser Ser Gly Tyr Tyr Leu Ser Pro Asn Asp Ala Phe Asp Ile
1               5                   10                  15

<210> SEQ ID NO 54
<211> LENGTH: 10
<212> TYPE: PRT
<213> ORGANISM: Artificial Sequence
<220> FEATURE:
<223> OTHER INFORMATION: Synthetic

<400> SEQUENCE: 54

Val Val Arg Phe Asn Asp Ala Phe Asp Ile
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic

<400> SEQUENCE: 55

Thr Met Leu Trp Asp Asp Ala Phe Asp Ile
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic

<400> SEQUENCE: 56

Gly Gly Tyr Tyr Gly Asp Asp Asp Ala Phe Asp Ile
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Synthetic

<400> SEQUENCE: 57

Arg His Trp Pro Gly Gly Phe Asp Tyr

```
<210> SEQ ID NO 58
<211> LENGTH: 10
<212> TYPE: PRT
<213> ORGANISM: Artificial Sequence
<220> FEATURE:
<223> OTHER INFORMATION: Synthetic

<400> SEQUENCE: 58

Val Cys Gly Tyr Asp Asp Ala Phe Asp Ile
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic

<400> SEQUENCE: 59

Gly Arg Val Gly Ala Thr Asn Arg Phe Gly Met Asp Val
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic

<400> SEQUENCE: 60

Glu Asp Phe Trp Ser Gly Tyr Gln Asp Val
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Synthetic

<400> SEQUENCE: 61

Ala Thr Val Lys Tyr Gly Gly Asp Asp Ala Phe Asp Ile
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic

<400> SEQUENCE: 62

Arg Thr Asp Ser Tyr Gly Tyr Ser Asp Ala Phe Asp Ile
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic

<400> SEQUENCE: 63

Val Ala Leu Trp Asp Asp Ala Phe Asp Ile
1               5                   10
```

```
<210> SEQ ID NO 64
<211> LENGTH: 13
<212> TYPE: PRT
<213> ORGANISM: Artificial Sequence
<220> FEATURE:
<223> OTHER INFORMATION: Synthetic

<400> SEQUENCE: 64

Ser Thr Val Lys Tyr Gly Ala Asp Asp Ala Phe Asp Ile
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic

<400> SEQUENCE: 65

Ala Ala Arg Ser Gly Tyr Tyr Asn Asp Tyr
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Synthetic

<400> SEQUENCE: 66

Gly Glu Lys Gly Tyr Ser Asn Ser Cys Ile Asp Tyr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic

<400> SEQUENCE: 67

Arg Ala Ser Gln Ser Ile Ser Ser Tyr Leu Asn
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic

<400> SEQUENCE: 68

Arg Ala Ser Gln Thr Ile Ser Arg Tyr Leu Asn
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Synthetic

<400> SEQUENCE: 69

Arg Ala Ser Gln Ser Ile Asp Thr Trp Leu Ala
1               5                   10
```

```
<210> SEQ ID NO 70
<211> LENGTH: 11
<212> TYPE: PRT
<213> ORGANISM: Artificial Sequence
<220> FEATURE:
<223> OTHER INFORMATION: Synthetic

<400> SEQUENCE: 70

Arg Ala Ser Glu Ser Ile Ser Ser Trp Leu Ala
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic

<400> SEQUENCE: 71

Arg Ala Ser Gln Ser Ile Ser Ser Trp Leu Ala
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic

<400> SEQUENCE: 72

Arg Ala Ser Gln Gly Ile Ser Ser Tyr Leu Ala
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic

<400> SEQUENCE: 73

Arg Ala Ser Gln Ser Ile Ser Thr Trp Leu Ala
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic

<400> SEQUENCE: 74

Arg Ala Ser Glu Ser Ile Ser Arg Trp Leu Ala
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic

<400> SEQUENCE: 75

Arg Ala Ser Gln Ser Ile Ser Asp Trp Leu Ala
1               5                   10
```

<210> SEQ ID NO 76
<211> LENGTH: 11
<212> TYPE: PRT
<213> ORGANISM: Artificial Sequence
<220> FEATURE:
<223> OTHER INFORMATION: Synthetic

<400> SEQUENCE: 76

Arg Ala Ser Arg Gly Ile Ser Ser Trp Leu Ala
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Synthetic

<400> SEQUENCE: 77

Arg Ala Ser Gln Gly Ile Ser Ser Trp Leu Ala
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Synthetic

<400> SEQUENCE: 78

Arg Ala Ser Gln Phe Ile Ser Lys Tyr Val Asn
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic

<400> SEQUENCE: 79

Gln Ala Ser Gln Asp Ile Ser Asn Tyr Leu Asn
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Synthetic

<400> SEQUENCE: 80

Ala Ala Ser Ser Leu Gln Ser
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic

<400> SEQUENCE: 81

Ala Thr Ser Ser Leu Gln Ser
1               5

<210> SEQ ID NO 82

```
<211> LENGTH: 7
<212> TYPE: PRT
<213> ORGANISM: Artificial Sequence
<220> FEATURE:
<223> OTHER INFORMATION: Synthetic

<400> SEQUENCE: 82

Asn Ala Ser Thr Leu Lys Ser
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic

<400> SEQUENCE: 83

Lys Ala Ser Ser Leu Glu Ser
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic

<400> SEQUENCE: 84

Ala Ala Ser Thr Leu Gln Ser
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic

<400> SEQUENCE: 85

Ala Ala Ser Asn Leu Glu Ser
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic

<400> SEQUENCE: 86

Lys Ala Ser Ser Leu Gln Ser
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic

<400> SEQUENCE: 87

Gly Ala Ser Ile Leu Glu Thr
1               5

<210> SEQ ID NO 88
<211> LENGTH: 7
```

```
<212> TYPE: PRT
<213> ORGANISM: Artificial Sequence
<220> FEATURE:
<223> OTHER INFORMATION: Synthetic

<400> SEQUENCE: 88

Asp Ala Ser Asn Leu Glu Thr
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic

<400> SEQUENCE: 89

Gln Gln Ser Tyr Ser Thr Pro Pro Thr
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic

<400> SEQUENCE: 90

Gln Gln Ser Tyr Ser Thr Pro Thr Thr
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic

<400> SEQUENCE: 91

Gln Gln Ser Tyr Ser Thr Pro Leu Thr
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic

<400> SEQUENCE: 92

Gln Gln Thr Tyr Ser Leu Pro Leu Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic

<400> SEQUENCE: 93

Gln Gln Tyr Leu Ser Val Pro Tyr Thr
1               5

<210> SEQ ID NO 94
<211> LENGTH: 9
<212> TYPE: PRT
```

<213> ORGANISM: Artificial Sequence
<220> FEATURE:
<223> OTHER INFORMATION: Synthetic

<400> SEQUENCE: 94

Gln Gln Ser Tyr Ser Ile Pro Leu Thr
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic

<400> SEQUENCE: 95

Gln Gln Ala Glu Ser Phe Pro Ser
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Ser Phe Ser Thr Pro Phe Thr
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic

<400> SEQUENCE: 97

Gln Gln Ser Ser Ser Ile Pro Leu Thr
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic

<400> SEQUENCE: 98

Gln Gln Ser Tyr Ser Thr Pro Phe Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic

<400> SEQUENCE: 99

Gln Gln Ala Asn Ser Phe Pro Phe Thr
1               5

<210> SEQ ID NO 100
<211> LENGTH: 10
<212> TYPE: PRT
<213> ORGANISM: Artificial Sequence

```
<220> FEATURE:
<223> OTHER INFORMATION: Synthetic

<400> SEQUENCE: 100

Gln Gln Thr His Ser Thr Pro Arg Gly Val
1               5                   10

<210> SEQ ID NO 101
<211> LENGTH: 9
<212> TYPE: PRT
<213> ORGANISM: Artificial Sequence
<220> FEATURE:
<223> OTHER INFORMATION: Synthetic

<400> SEQUENCE: 101

Gln His Ser Asn Ser Leu Pro Leu Thr
1               5

<210> SEQ ID NO 102
<211> LENGTH: 10
<212> TYPE: PRT
<213> ORGANISM: Artificial Sequence
<220> FEATURE:
<223> OTHER INFORMATION: Synthetic

<400> SEQUENCE: 102

Gln Gln Tyr Asp Asn Leu Pro Pro Phe Thr
1               5                   10

<210> SEQ ID NO 103
<211> LENGTH: 7
<212> TYPE: PRT
<213> ORGANISM: Artificial Sequence
<220> FEATURE:
<223> OTHER INFORMATION: Synthetic

<400> SEQUENCE: 103

Gly Phe Thr Leu Ser Ser His
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic

<400> SEQUENCE: 104

Gly Phe Thr Phe Ser Thr Tyr
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic

<400> SEQUENCE: 105

Gly Phe Ser Phe Ser Ser Tyr
1               5

<210> SEQ ID NO 106
<211> LENGTH: 7
<212> TYPE: PRT
<213> ORGANISM: Artificial Sequence
<220> FEATURE:
```

```
<223> OTHER INFORMATION: Synthetic

<400> SEQUENCE: 106

Gly Phe Thr Phe Ser Ser Tyr
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic

<400> SEQUENCE: 107

Gly Phe Thr Phe Ser Asp Ser
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic

<400> SEQUENCE: 108

Gly Phe Thr Phe Ser Asp His
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic

<400> SEQUENCE: 109

Gly Gly Thr Phe Ser Ser Tyr
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic

<400> SEQUENCE: 110

Gly Phe Thr Phe Ser Val Tyr
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic

<400> SEQUENCE: 111

Gly Phe Thr Phe Ser Ser Asn
1               5

<210> SEQ ID NO 112
<211> LENGTH: 6
<212> TYPE: PRT
<213> ORGANISM: Artificial Sequence
<220> FEATURE:
<223> OTHER INFORMATION: Synthetic
```

<400> SEQUENCE: 112

His Gln Asp Ala Ser Leu
1               5

<210> SEQ ID NO 113
<211> LENGTH: 6
<212> TYPE: PRT
<213> ORGANISM: Artificial Sequence
<220> FEATURE:
<223> OTHER INFORMATION: Synthetic

<400> SEQUENCE: 113

Ala Ala Ser Gly Asp Tyr
1               5

<210> SEQ ID NO 114
<211> LENGTH: 6
<212> TYPE: PRT
<213> ORGANISM: Artificial Sequence
<220> FEATURE:
<223> OTHER INFORMATION: Synthetic

<400> SEQUENCE: 114

Lys Glu Asp Gly Ser Glu
1               5

<210> SEQ ID NO 115
<211> LENGTH: 6
<212> TYPE: PRT
<213> ORGANISM: Artificial Sequence
<220> FEATURE:
<223> OTHER INFORMATION: Synthetic

<400> SEQUENCE: 115

Lys Gln Asp Gly Ser Glu
1               5

<210> SEQ ID NO 116
<211> LENGTH: 6
<212> TYPE: PRT
<213> ORGANISM: Artificial Sequence
<220> FEATURE:
<223> OTHER INFORMATION: Synthetic

<400> SEQUENCE: 116

Ser Pro Tyr Gly Gly Ser
1               5

<210> SEQ ID NO 117
<211> LENGTH: 6
<212> TYPE: PRT
<213> ORGANISM: Artificial Sequence
<220> FEATURE:
<223> OTHER INFORMATION: Synthetic

<400> SEQUENCE: 117

Ser Ser Ser Ser Ser Tyr
1               5

<210> SEQ ID NO 118
<211> LENGTH: 6
<212> TYPE: PRT
<213> ORGANISM: Artificial Sequence
<220> FEATURE:
<223> OTHER INFORMATION: Synthetic

```
<400> SEQUENCE: 118

Ile Pro Ile Phe Gly Thr
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic

<400> SEQUENCE: 119

Ser Asn Gly Asp Gly Asp Ile
1               5

<210> SEQ ID NO 120
<211> LENGTH: 6
<212> TYPE: PRT
<213> ORGANISM: Artificial Sequence
<220> FEATURE:
<223> OTHER INFORMATION: Synthetic

<400> SEQUENCE: 120

Gly Gly Gly Gly Val Asn
1               5

<210> SEQ ID NO 121
<211> LENGTH: 118
<212> TYPE: PRT
<213> ORGANISM: Artificial Sequence
<220> FEATURE:
<223> OTHER INFORMATION: Synthetic

<400> SEQUENCE: 121

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 122
<211> LENGTH: 118
<212> TYPE: PRT
<213> ORGANISM: Artificial Sequence
<220> FEATURE:
<223> OTHER INFORMATION: Synthetic

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Glu Ser
```

```
                    20                  25                  30
Trp Ile His Trp Val Arg Gln Ala Pro Gly Lys Gly Leu Glu Trp Val
            35                  40                  45
Ala Trp Ile Ser Pro Tyr Gly Ser Thr Tyr Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Arg His Trp Pro Gly Gly Phe Asp Tyr Trp Gly Gln Gly Thr
            100                 105                 110
Leu Val Thr Val Ser Ser
        115
```

<210> SEQ ID NO 123
<211> LENGTH: 118
<212> TYPE: PRT
<213> ORGANISM: Artificial Sequence
<220> FEATURE:
<223> OTHER INFORMATION: Synthetic

<400> SEQUENCE: 123

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Glu Ser
            20                  25                  30
Trp Ile His Trp Val Arg Gln Ala Pro Gly Lys Gly Leu Glu Trp Val
        35                  40                  45
Ala Trp Ile Ser Pro Tyr Gly Ser Thr Tyr Tyr Ala Asp Ala Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Arg His Trp Pro Gly Gly Phe Asp Tyr Trp Gly Gln Gly Thr
            100                 105                 110
Leu Val Thr Val Ser Ser
        115
```

<210> SEQ ID NO 124
<211> LENGTH: 119
<212> TYPE: PRT
<213> ORGANISM: Artificial Sequence
<220> FEATURE:
<223> OTHER INFORMATION: Synthetic

<400> SEQUENCE: 124

```
Gln Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Trp Met Ser Trp Val Arg Gln Ala Pro Gly Lys Gly Leu Glu Trp Val
        35                  40                  45
Ala Asn Ile Lys Gln Asp Gly Ser Glu Lys Tyr Tyr Val Asp Ser Val
    50                  55                  60
Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Val Ala Leu Trp Asp Asp Ala Phe Asp Ile Trp Gly Gln Gly
            100                 105                 110

Thr Met Val Thr Val Ser Ser
        115

<210> SEQ ID NO 125
<211> LENGTH: 107
<212> TYPE: PRT
<213> ORGANISM: Artificial Sequence
<220> FEATURE:
<223> OTHER INFORMATION: Synthetic

<400> SEQUENCE: 125

Asp Ile Gln Met Thr Gln Ser Pro Ser Thr Leu Ser Ala Ser Val Gly
1               5                   10                  15

Asp Arg Val Ile Ile Thr Cys Arg Ala Ser Arg Gly Ile Ser Ser Trp
            20                  25                  30

Leu Ala Trp Tyr Gln Gln Lys Pro Gly Lys Ala Pro Asn Leu Leu Ile
        35                  40                  45

Ser Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ile Pro Leu
                85                  90                  95

Thr Phe Gly Gly Gly Thr Lys Val Glu Ile Lys
        100                 105

<210> SEQ ID NO 126
<211> LENGTH: 119
<212> TYPE: PRT
<213> ORGANISM: Artificial Sequence
<220> FEATURE:
<223> OTHER INFORMATION: Synthetic

<400> SEQUENCE: 126

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Glu Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Ala Leu Trp Asp Asp Ala Phe Asp Ile Trp Gly Gln Gly
            100                 105                 110

Thr Met Val Thr Val Ser Ser
        115

<210> SEQ ID NO 127
<211> LENGTH: 119
<212> TYPE: PRT
<213> ORGANISM: Artificial Sequence
```

<220> FEATURE:
<223> OTHER INFORMATION: Synthetic

<400> SEQUENCE: 127

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Ala Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Ala Leu Trp Asp Asp Ala Phe Asp Ile Trp Gly Gln Gly
            100                 105                 110

Thr Met Val Thr Val Ser Ser
        115

<210> SEQ ID NO 128
<211> LENGTH: 119
<212> TYPE: PRT
<213> ORGANISM: Artificial Sequence
<220> FEATURE:
<223> OTHER INFORMATION: Synthetic

<400> SEQUENCE: 128

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Ala Leu Trp Asp Asp Ala Phe Asp Ile Trp Gly Gln Gly
            100                 105                 110

Thr Met Val Thr Val Ser Ser
        115

<210> SEQ ID NO 129
<211> LENGTH: 107
<212> TYPE: PRT
<213> ORGANISM: Artificial Sequence
<220> FEATURE:
<223> OTHER INFORMATION: Synthetic

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

```
Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln His Ser Asn Ala Leu Pro Leu
                 85                  90                  95

Thr Phe Gly Gly Gly Thr Lys Val Glu Ile Lys
            100                 105
```

<210> SEQ ID NO 130
<211> LENGTH: 119
<212> TYPE: PRT
<213> ORGANISM: Artificial Sequence
<220> FEATURE:
<223> OTHER INFORMATION: Synthetic

<400> SEQUENCE: 130

```
Gln Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
            35                  40                  45

Ala Asn Ile Lys Gln Asp Ala Ser Glu Lys Tyr Tyr Val Glu Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Val Ala Leu Trp Asp Asp Ala Phe Asp Ile Trp Gly Gln Gly
            100                 105                 110

Thr Met Val Thr Val Ser Ser
            115
```

<210> SEQ ID NO 131
<211> LENGTH: 107
<212> TYPE: PRT
<213> ORGANISM: Artificial Sequence
<220> FEATURE:
<223> OTHER INFORMATION: Synthetic

<400> SEQUENCE: 131

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln His Ser Gln Ser Leu Pro Leu
                 85                  90                  95

Thr Phe Gly Gly Gly Thr Lys Val Glu Ile Lys
            100                 105
```

<210> SEQ ID NO 132
<211> LENGTH: 5
<212> TYPE: PRT
<213> ORGANISM: Artificial Sequence
<220> FEATURE:
<223> OTHER INFORMATION: Synthetic

<400> SEQUENCE: 132

Glu Ser Trp Ile His
1               5

<210> SEQ ID NO 133
<211> LENGTH: 17
<212> TYPE: PRT
<213> ORGANISM: Artificial Sequence
<220> FEATURE:
<223> OTHER INFORMATION: Synthetic

<400> SEQUENCE: 133

Trp Ile Ser Pro Tyr Gly Gly Ser Thr Tyr Tyr Ala Asp Ala Val Lys
1               5                   10                  15

Gly

<210> SEQ ID NO 134
<211> LENGTH: 17
<212> TYPE: PRT
<213> ORGANISM: Artificial Sequence
<220> FEATURE:
<223> OTHER INFORMATION: Synthetic

<400> SEQUENCE: 134

Trp Ile Ser Pro Tyr Gly Gly Ser Thr Tyr Tyr Ala Glu Ser Val Lys
1               5                   10                  15

Gly

<210> SEQ ID NO 135
<211> LENGTH: 17
<212> TYPE: PRT
<213> ORGANISM: Artificial Sequence
<220> FEATURE:
<223> OTHER INFORMATION: Synthetic

<400> SEQUENCE: 135

Asn Ile Lys Gln Asp Gly Ser Glu Lys Tyr Tyr Val Glu Ser Val Lys
1               5                   10                  15

Gly

<210> SEQ ID NO 136
<211> LENGTH: 17
<212> TYPE: PRT
<213> ORGANISM: Artificial Sequence
<220> FEATURE:
<223> OTHER INFORMATION: Synthetic

<400> SEQUENCE: 136

Asn Ile Lys Gln Asp Ala Ser Glu Lys Tyr Tyr Val Asp Ser Val Lys
1               5                   10                  15

Gly

<210> SEQ ID NO 137
<211> LENGTH: 17
<212> TYPE: PRT
<213> ORGANISM: Artificial Sequence
<220> FEATURE:
<223> OTHER INFORMATION: Synthetic

<400> SEQUENCE: 137

Asn Ile Lys Gln Asp Ala Ser Glu Lys Tyr Tyr Val Glu Ser Val Lys
1               5                   10                  15

Gly

<210> SEQ ID NO 138
<211> LENGTH: 9
<212> TYPE: PRT
<213> ORGANISM: Artificial Sequence
<220> FEATURE:
<223> OTHER INFORMATION: Synthetic

<400> SEQUENCE: 138

Gln His Ser Asn Ala Leu Pro Leu Thr
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic

<400> SEQUENCE: 139

Gln His Ser Gln Ser Leu Pro Leu Thr
1               5

<210> SEQ ID NO 140
<211> LENGTH: 119
<212> TYPE: PRT
<213> ORGANISM: Artificial Sequence
<220> FEATURE:
<223> OTHER INFORMATION: Synthetic

<400> SEQUENCE: 140

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Glu Gly Ser Glu Lys Tyr Tyr Val Asp Ala Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Ala Leu Trp Asp Asp Ala Phe Asp Ile Trp Gly Gln Gly
            100                 105                 110

Thr Met Val Thr Val Ser Ser
        115

<210> SEQ ID NO 141
<211> LENGTH: 7
<212> TYPE: PRT
<213> ORGANISM: Artificial Sequence
<220> FEATURE:
<223> OTHER INFORMATION: Synthetic

<400> SEQUENCE: 141

```
Gly Phe Thr Phe Ser Glu Ser
1               5

<210> SEQ ID NO 142
<211> LENGTH: 6
<212> TYPE: PRT
<213> ORGANISM: Artificial Sequence
<220> FEATURE:
<223> OTHER INFORMATION: Synthetic

<400> SEQUENCE: 142

Lys Gln Asp Ala Ser Glu
1               5

<210> SEQ ID NO 143
<211> LENGTH: 17
<212> TYPE: PRT
<213> ORGANISM: Artificial Sequence
<220> FEATURE:
<223> OTHER INFORMATION: Synthetic

<400> SEQUENCE: 143

Asn Ile Lys Gln Glu Gly Ser Glu Lys Tyr Tyr Val Asp Ser Val Lys
1               5                   10                  15

Gly

<210> SEQ ID NO 144
<211> LENGTH: 17
<212> TYPE: PRT
<213> ORGANISM: Artificial Sequence
<220> FEATURE:
<223> OTHER INFORMATION: Synthetic

<400> SEQUENCE: 144

Asn Ile Lys Gln Glu Gly Ser Glu Lys Tyr Tyr Val Asp Ala Val Lys
1               5                   10                  15

Gly

<210> SEQ ID NO 145
<211> LENGTH: 119
<212> TYPE: PRT
<213> ORGANISM: Artificial Sequence
<220> FEATURE:
<223> OTHER INFORMATION: Synthetic

<400> SEQUENCE: 145

Gln Val Gln Leu Leu Asp Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg Val Ala Leu Trp Asp Asp Ala Phe Asp Ile Trp Gly Gln Gly
            100                 105                 110

Thr Met Val Thr Val Ser Ser
            115
```